(12) United States Patent
Burke et al.

(10) Patent No.: US 7,101,962 B2
(45) Date of Patent: Sep. 5, 2006

(54) ANTIBODIES OF THE P2Y10 RECEPTOR USEFUL IN ALTERING T LYMPHOCYTE FUNCTION

(75) Inventors: James R. Burke, Upper Holland, PA (US); Violetta Iotzova, Robbinsville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/844,736

(22) Filed: May 13, 2004

(65) Prior Publication Data

US 2004/0247599 A1 Dec. 9, 2004

Related U.S. Application Data

(60) Provisional application No. 60/471,135, filed on May 15, 2003.

(51) Int. Cl.
*A61K 39/395* (2006.01)
(52) U.S. Cl. .................. 530/143.1; 424/139.1; 424/141.1; 530/387.9; 530/388.1; 530/388.22; 435/331; 435/334
(58) Field of Classification Search ............ 530/387.9, 530/388.1, 388.22; 424/139.1, 143.1; 435/326
See application file for complete search history.

(56) References Cited

U.S. PATENT DOCUMENTS

| 5,834,587 A | 11/1998 | Chan et al. |
| 2003/0113798 A1* | 6/2003 | Burmer et al. ............... 435/7.1 |
| 2004/0048817 A1* | 3/2004 | Emtage et al. ............... 514/44 |

OTHER PUBLICATIONS

Wise et al., "Target validation of G-protein coupled receptors," (2002) Drug Discovery Today, 7:235-246.*
Harlow et al. "Antibodies, A Laboratory Manual," (1998) Cold Spring Harbor Laboratory, p. 76.*
Kuby, J. Immunology, 1991, W. H. Freeman and Company, p. 125.*
NCBI Accession No. AF000545 (gi:2104786), Bohm, S.K., May 17, 1997.
Coughlin, Shaun, R., "Expanding horizons for receptors coupled to G proteins: diversity and disease", Curr. Opin. Cell Biol., vol. 6, pp. 191-197 (1994).
Strosberg, Arthur, D. "Structure/function relationship of proteins belonging to the family of receptors coupled to GTP-binding proteins", Eur. J. Biochem, vol. 196, pp. 1-10 (1991).
Feng, et al., "HIV-1 Entry Cofactor: Functional cDNA Cloning of a Seven-Transmembrane, G Protein-Coupled Receptor", Science, vol. 272, pp. 872-877 (1996).
Starling, et al., "Characterization of mouse CD6 with novel monoclonal antibodies which enhance the allogeneic mixed leukocyte reaction", Eur. J. Immunol., vol. 26, pp. 738-746 (1996).
Horn, et al., "G protein-coupled receptors *in silico*", J. Mol. Med., vol. 76, pp. 464-468 (1998).
Rao, et al., "The Ets Factors PU.1 and Spi-B Regulate the Transcription *in Vivo* of P2Y10, a Lymphoid Restricted Heptahelical Receptor", J. of Biol. Chem., vol. 274 (48), pp. 34245-34252 (1999).
Ledbetter, et al., "Valency of CD3 Binding and Internalization of the CD3 Cell-Surface Complex Control T Cell Responses to Second Signals: Distinction Between Effects on Protein Kinase C, Cytoplasmic Free Calcium, and Proliferation", J. of Immunol., vol. 136 (11) pp. 3945-3952 (1986).
Martin, et al., "A 44 Kilodalton Cell Surface Homodimer Regulates Interleukin 2 Production by Activated Human T Lymphocytes", J. of Immunol., vol. 136 (9), pp. 3282-3287 (1986).

* cited by examiner

*Primary Examiner*—Patrick J. Nolan
*Assistant Examiner*—Michael Szperka
(74) *Attorney, Agent, or Firm*—Eve L. Frank; John A. Lamerdin

(57) ABSTRACT

The present invention relates to modulators of P2Y10. Various modulators are disclosed, including an antibody that binds specifically to P2Y10. The present invention also relates to methods of activating resting T lymphocytes and inhibiting the proliferation of activated T lymphocytes. Methods of upregulating trascription of P2Y10 mRNA in a resting T lymphocyte, methods of inducing expression of P2Y10 on the surface of a resting T lymphocyte and methods of activating a T lymphocyte are disclosed. Also disclosed are pharmaceuticals and methods of treating an immune disease.

2 Claims, 2 Drawing Sheets

SEQUENCE LISTING

```
<160> NUMBER OF SEQ ID NOS: 8

<210> SEQ ID NO 1
<211> LENGTH: 1020
<212> TYPE: DNA
<213> ORGANISM: Homo sapiens
<220> FEATURE:
<221> NAME/KEY: CDS
<222> LOCATION: (1)..(1020)

<400> SEQUENCE: 1 atg gct aac ctt gac aaa tac act gaa aca ttc aag atg ggt agc aac      48
Met Ala Asn Leu Asp Lys Tyr Thr Glu Thr Phe Lys Met Gly Ser Asn
1               5                   10                  15 agt acc agc act gct gag att tac tgt aat gtc act aat gtg aaa ttt      96
Ser Thr Ser Thr Ala Glu Ile Tyr Cys Asn Val Thr Asn Val Lys Phe
                20                  25                  30 caa tac tcc ctc tat gca acc acc tat atc ctc ata ttc att cct ggt     144
Gln Tyr Ser Leu Tyr Ala Thr Thr Tyr Ile Leu Ile Phe Ile Pro Gly
            35                  40                  45 ctt ctg gct aac agt gca gcc ttg tgg gtt ctg tgc cgc ttc atc agc     192
Leu Leu Ala Asn Ser Ala Ala Leu Trp Val Leu Cys Arg Phe Ile Ser
        50                  55                  60 aag aaa aat aaa gcc atc att ttc atg atc aac ctc tct gtg gct gac     240
Lys Lys Asn Lys Ala Ile Ile Phe Met Ile Asn Leu Ser Val Ala Asp
65                  70                  75                  80 ctt gct cat gta tta tct tta ccc ctc cgg att tac tat tac atc agc     288
Leu Ala His Val Leu Ser Leu Pro Leu Arg Ile Tyr Tyr Tyr Ile Ser
                85                  90                  95
```

```
cac cac tgg cct ttc cag aga gcc ctt tgc ctg ctc tgc ttc tac ctg        336
His His Trp Pro Phe Gln Arg Ala Leu Cys Leu Leu Cys Phe Tyr Leu
            100                 105                 110 aag tat ctc aac atg tat gcc agc att tgt ttc ctg acg tgc atc agt        384
Lys Tyr Leu Asn Met Tyr Ala Ser Ile Cys Phe Leu Thr Cys Ile Ser
        115                 120                 125 ctt caa agg tgc ttt ttt ctc ctc aag ccc ttc agg gcc aga gac tgg        432
Leu Gln Arg Cys Phe Phe Leu Leu Lys Pro Phe Arg Ala Arg Asp Trp
130                 135                 140 aag cgt agg tac gat gtg ggc atc agt gct gcc atc tgg atc gtt gtg        480
Lys Arg Arg Tyr Asp Val Gly Ile Ser Ala Ala Ile Trp Ile Val Val
145                 150                 155                 160 ggg act gcc tgt ttg cca ttt ccc atc ctg aga agc aca gac tta aac        528
Gly Thr Ala Cys Leu Pro Phe Pro Ile Leu Arg Ser Thr Asp Leu Asn
                165                 170                 175 aac aac aag tcc tgc ttt gct gat ctt gga tac aag caa atg aat gca        576
Asn Asn Lys Ser Cys Phe Ala Asp Leu Gly Tyr Lys Gln Met Asn Ala
            180                 185                 190 gtt gcg ttg gtc ggg atg att aca gtt gct gag ctt gca gga ttt gtg        624
Val Ala Leu Val Gly Met Ile Thr Val Ala Glu Leu Ala Gly Phe Val
        195                 200                 205 atc cca gtg atc atc atc gca tgg tgt acc tgg aaa act act ata tcc        672
Ile Pro Val Ile Ile Ile Ala Trp Cys Thr Trp Lys Thr Thr Ile Ser
    210                 215                 220 ttg aga cag cca cca atg gct ttc caa ggg atc agt gag agg cag aaa        720
Leu Arg Gln Pro Pro Met Ala Phe Gln Gly Ile Ser Glu Arg Gln Lys
225                 230                 235                 240 gca ctg cgg atg gtg ttc atg tgt gct gca gtc ttc ttc atc tgc ttc        768
Ala Leu Arg Met Val Phe Met Cys Ala Ala Val Phe Phe Ile Cys Phe
                245                 250                 255 act ccc tat cat att aac ttt att ttt tac acc atg gta aag gaa acc        816
Thr Pro Tyr His Ile Asn Phe Ile Phe Tyr Thr Met Val Lys Glu Thr
            260                 265                 270 atc att agc agt tgt ccc gtt gtc cga atc gca ctg tat ttc cac cct        864
Ile Ile Ser Ser Cys Pro Val Val Arg Ile Ala Leu Tyr Phe His Pro
        275                 280                 285 ttt tgc ctg tgc ctt gca agt ctc tgc tgc ctt ttg gat cca att ctt        912
Phe Cys Leu Cys Leu Ala Ser Leu Cys Cys Leu Leu Asp Pro Ile Leu
    290                 295                 300 tat tac ttt atg gct tca gag ttt cgt gac caa cta tcc cgc cat ggc        960
Tyr Tyr Phe Met Ala Ser Glu Phe Arg Asp Gln Leu Ser Arg His Gly
305                 310                 315                 320 agt tct gtg acc cgc tcc cgc ctc atg agc aag gag agt ggt tca tca       1008
Ser Ser Val Thr Arg Ser Arg Leu Met Ser Lys Glu Ser Gly Ser Ser
                325                 330                 335 atg att ggc taa                                                        1020
Met Ile Gly <210> SEQ ID NO 2
<211> LENGTH: 339
<212> TYPE: PRT
<213> ORGANISM: Homo sapiens

<400> SEQUENCE: 2

Met Ala Asn Leu Asp Lys Tyr Thr Glu Thr Phe Lys Met Gly Ser Asn
1               5                   10                  15

Ser Thr Ser Thr Ala Glu Ile Tyr Cys Asn Val Thr Asn Val Lys Phe
            20                  25                  30

Gln Tyr Ser Leu Tyr Ala Thr Thr Tyr Ile Leu Ile Phe Ile Pro Gly
        35                  40                  45
```

```
Leu Leu Ala Asn Ser Ala Ala Leu Trp Val Leu Cys Arg Phe Ile Ser
 50                  55                  60

Lys Lys Asn Lys Ala Ile Ile Phe Met Ile Asn Leu Ser Val Ala Asp
 65                  70                  75                  80

Leu Ala His Val Leu Ser Leu Pro Leu Arg Ile Tyr Tyr Tyr Ile Ser
                 85                  90                  95

His His Trp Pro Phe Gln Arg Ala Leu Cys Leu Leu Cys Phe Tyr Leu
            100                 105                 110

Lys Tyr Leu Asn Met Tyr Ala Ser Ile Cys Phe Leu Thr Cys Ile Ser
            115                 120                 125

Leu Gln Arg Cys Phe Phe Leu Leu Lys Pro Phe Arg Ala Arg Asp Trp
            130                 135                 140

Lys Arg Arg Tyr Asp Val Gly Ile Ser Ala Ala Ile Trp Ile Val Val
145                 150                 155                 160

Gly Thr Ala Cys Leu Pro Phe Pro Ile Leu Arg Ser Thr Asp Leu Asn
                165                 170                 175

Asn Asn Lys Ser Cys Phe Ala Asp Leu Gly Tyr Lys Gln Met Asn Ala
            180                 185                 190

Val Ala Leu Val Gly Met Ile Thr Val Ala Glu Leu Ala Gly Phe Val
            195                 200                 205

Ile Pro Val Ile Ile Ala Trp Cys Thr Trp Lys Thr Thr Ile Ser
210                 215                 220

Leu Arg Gln Pro Pro Met Ala Phe Gln Gly Ile Ser Glu Arg Gln Lys
225                 230                 235                 240

Ala Leu Arg Met Val Phe Met Cys Ala Ala Val Phe Ile Cys Phe
                245                 250                 255

Thr Pro Tyr His Ile Asn Phe Ile Phe Tyr Thr Met Val Lys Glu Thr
                260                 265                 270

Ile Ile Ser Ser Cys Pro Val Val Arg Ile Ala Leu Tyr Phe His Pro
            275                 280                 285

Phe Cys Leu Cys Leu Ala Ser Leu Cys Cys Leu Leu Asp Pro Ile Leu
            290                 295                 300

Tyr Tyr Phe Met Ala Ser Glu Phe Arg Asp Gln Leu Ser Arg His Gly
305                 310                 315                 320

Ser Ser Val Thr Arg Ser Arg Leu Met Ser Lys Glu Ser Gly Ser Ser
                325                 330                 335

Met Ile Gly

<210> SEQ ID NO 3
<211> LENGTH: 21
<212> TYPE: PRT
<213> ORGANISM: Homo sapiens

<400> SEQUENCE: 3

Arg Ser Thr Asp Leu Asn Asn Lys Ser Cys Phe Ala Asp Leu Gly
1               5                   10                  15

Tyr Lys Gln Met Asn
            20

<210> SEQ ID NO 4
<211> LENGTH: 22
<212> TYPE: PRT
<213> ORGANISM: Artificial
<220> FEATURE:
<223> OTHER INFORMATION: P2Y10 residues 171-191 with terminal cysteine
      added
```

-continued

```
<400> SEQUENCE: 4

Arg Ser Thr Asp Leu Asn Asn Asn Lys Ser Cys Phe Ala Asp Leu Gly
1               5                   10                  15

Tyr Lys Gln Met Asn Cys
            20

<210> SEQ ID NO 5
<211> LENGTH: 21
<212> TYPE: DNA
<213> ORGANISM: Artificial
<220> FEATURE:
<223> OTHER INFORMATION: Synthesized primer

<400> SEQUENCE: 5
catctgcttc actccctatc a                                          21

<210> SEQ ID NO 6
<211> LENGTH: 20
<212> TYPE: DNA
<213> ORGANISM: Artificial
<220> FEATURE:
<223> OTHER INFORMATION: Synthesized primer

<400> SEQUENCE: 6
cattgatgaa ccactctcct                                            20

<210> SEQ ID NO 7
<211> LENGTH: 19
<212> TYPE: DNA
<213> ORGANISM: Artificial
<220> FEATURE:
<223> OTHER INFORMATION: Synthesized primer

<400> SEQUENCE: 7
ttagcacccc tggccaagg                                             19

<210> SEQ ID NO 8
<211> LENGTH: 20
<212> TYPE: DNA
<213> ORGANISM: Artificial
<220> FEATURE:
<223> OTHER INFORMATION: Synthesized primer

<400> SEQUENCE: 8
cttactcctt ggaggccatg                                            20
```

US 7,101,962 B2

ANTIBODIES OF THE P2Y10 RECEPTOR USEFUL IN ALTERING T LYMPHOCYTE FUNCTION

The present patent application claims the benefit of U.S. Provisional Patent Application Ser. No. 60/471,135, filed May 15, 2003, the disclosure of which is incorporated herein by reference in its entirety.

FIELD OF THE INVENTION

The present invention generally relates to method of modulating the biological activity of a T lymphocyte via a binding event comprising a P2Y10 receptor. More particularly, the present invention relates to a method of modulating the biological activity of a T lymphocyte via a binding event comprising binding of a P2Y10 receptor by an antibody. The present invention also relates to modulators, including antibodies, adapted to bind a P2Y10 receptor and to modulate T lymphocyte biological activity.

BACKGROUND OF THE INVENTION

T lymphocytes mediate immune system function by recognizing membrane antigen on antigen-presenting cells, virus-infected cells, cancer cells, and grafts. Binding of antigen to T lymphocytes either causes the cells to proliferate and secrete various cytokines, which activates an immune response, or causes the T lymphocyte to acquire cytotoxic activity to aid in the immune response.

While essential to the immune response, aberrant T cell responses have been implicated in a number of disorders. For instance, autoimmune diseases such as rheumatoid arthritis and multiple sclerosis are thought to result, in part, from T cells recognizing self antigens as foreign. Conversely, dampened immune/T cell responses may play a role in some malignant cancers.

G-protein-coupled receptors (GPCRs) are of great biological significance, as the malfunction of GPCRs has been implicated in the onset of many diseases, including, but not limited to, Alzheimer's, Parkinson, diabetes, dwarfism, color blindness, retinal pigmentosa and asthma. Also, GPCRs have also been implicated in depression, schizophrenia, sleeplessness, hypertension, anxiety, stress, renal failure and in several cardiovascular, metabolic, neurologic, oncology-related and immune disorders (Horn & Vriend, (1998) *J. Mol. Med.* 76: 464–468). GPCRs have also been shown to play a role in HIV infection (Feng et al., (1996) *Science* 272:872–877).

GPCRs are integral membrane proteins characterized by the presence of seven hydrophobic transmembrane domains that together form a bundle of antiparallel alpha ($\alpha$) helices. The 7 transmembrane regions are designated as TM1, TM2, TM3, TM4, TM5, TM6, and TM7. These proteins range in size from under 400 to over 1000 amino acids (Strosberg, (1991) *Eur. J. Biochem.* 196:110; Coughlin, (1994) *Curr. Opin. Cell Biol.* 6:191–197). The amino-terminus of a GPCR is extracellular, is of variable length, and is often glycosylated. The carboxy-terminus is cytoplasmic and generally phosphorylated. Extracellular loops of GPCRs alternate with intracellular loops and link the transmembrane domains. Cysteine disulfide bridges linking the second and third extracellular loops may interact with agonists and antagonists. The most conserved domains of GPCRs are the transmembrane domains and the first two cytoplasmic loops. The transmembrane domains account for structural and functional features of the receptor. In some G-protein coupled receptors, the bundle of $\alpha$ helices forms a ligand-binding pocket formed by several G-protein coupled receptor transmembrane domains.

P2Y10 (GenBank Accession Number AF000545; SEQ ID NOs:1 and 2) is a putative 7-transmembrane GPCR that appears to show lymphoid-restricted expression (Rao et al., (1999) *J. Biol. Chem.* 274:34245–34252). Indeed, northern blot analysis of RNA showed P2Y10 expression in B and T cells with undetectable levels in macrophages and fibroblasts. In mice, the P2Y10 promoter contains a PU.1/Spi-B binding site required for P2Y10 transcription. Although it is not the present inventors' intention to be bound by any particular theory of operation, because the PU.1 and Spi-B transcription factors have been implicated in B cell receptor signaling in mice (Rao et al., (1999) *J. Biol. Chem.* 274: 34245–34252), the present inventors speculated there is a connection between B cell receptor signaling and P2Y10 in humans. The present inventors further speculated there is a connection between T cell receptor signaling and P2Y10 in humans.

Presently, the structure and function of P2Y10 is under investigation. For example, U.S. Pat. No. 5,834,587 to Chan et al. discloses the identification of the human G-protein-coupled receptor called HLTEX11 and the cloning of the gene encoding the same. Human HLTEX11 is also known as P2Y10 and for clarity and consistency, throughout the present disclosure the term P2Y10 is used to describe this polypeptide. As noted, Chan et al. disclose a nucleic acid sequence encoding a human P2Y10 polypeptide, as well as an amino acid sequence of the same. However, Chan et al. do not disclose modulating T lymphocyte activity by employing an antibody directed against a P2Y10 polypeptide having one or more of the following properties: (a) the ability to activate a resting T lymphocyte; (b) the ability to induce surface expression of P2Y10 on a resting T lymphocyte; (c) the ability to stimulate P2Y10 mRNA expression in a resting T lymphocyte; and (d) the ability to inhibit proliferation of an activated T lymphocyte.

Thus, although a nucleic acid sequence encoding a human P2Y10 polypeptide, as well as an amino acid sequence of a human P2Y10 polypeptide, is known, until the present disclosure, a modulator of T lymphocyte function that interacts with P2Y10 and has different functions depending on the state of the T lymphocyte has not been described. Therefore, what is needed is a modulator of T lymphocyte function that interacts with a P2Y10 polypeptide, for example an anti-P2Y10 antibody. Such a T lymphocyte modulator could be employed as a therapeutic agent, as a component of a therapeutic agent, as a component of a diagnostic method or as a component of a diagnostic or therapeutic kit. As described more fully herein below, the present invention solves this and other problems.

SUMMARY OF THE INVENTION

A P2Y10 modulator is disclosed. In one embodiment, the modulator associates specifically with a P2Y10 polypeptide and has one or more properties selected from the group consisting of: (a) the ability to activate a resting T lymphocyte upon association with a P2Y10 polypeptide; (b) the ability to induce expression of a P2Y10 polypeptide on the surface of a resting T lymphocyte upon association with a P2Y10 polypeptide; (c) the ability to stimulate expression of mRNA encoding a P2Y10 polypeptide in a resting T lymphocyte upon association with a P2Y10 polypeptide; and (d) the ability to inhibit proliferation of an activated T lymphocyte upon association with a P2Y10 polypeptide. The modulator can associate specifically with residues 171–191 of a P2Y10 polypeptide (RSTDLNNNKSCFADLGYKQMN; SEQ ID NO:3). Additionally, the modulator can comprise an antibody, for example a monoclonal antibody, such as a monoclonal antibody produced by the hybridoma strain identified as ATCC accession number PTA-3975.

Further, an isolated antibody that associates specifically with a P2Y10 polypeptide is disclosed. In one embodiment, the antibody and has one or more properties selected from the group consisting of: (a) the ability to activate a resting T lymphocyte upon association with a P2Y10 polypeptide; (b) the ability to induce expression of a P2Y10 polypeptide on the surface of a resting T lymphocyte upon association with a P2Y10 polypeptide; (c) the ability to stimulate expression of mRNA encoding a P2Y10 polypeptide in a resting T lymphocyte upon association with a P2Y10 polypeptide; and (d) the ability to inhibit proliferation of an activated T lymphocyte upon association with a P2Y10 polypeptide. In other embodiments, the antibody can associate specifically with residues 171–191 of a P2Y10 polypeptide (SEQ ID NOs:3 and 4) and/or can be a monoclonal antibody, such as a monoclonal antibody produced by the hybridoma strain identified as ATCC accession number PTA-3975.

A method of activating a resting T lymphocyte is also disclosed. In one embodiment, the method comprises contacting a resting T lymphocyte with a modulator of a P2Y10 polypeptide. In other embodiments, the modulator associates specifically with residues 171–191 of a P2Y10 polypeptide (SEQ ID NOs:3 and 4), and/or the modulator is an antibody, for example a monoclonal antibody, and/or is produced by the hybridoma strain identified as ATCC accession number PTA-3975.

Additionally, a method of inducing expression of a P2Y10 polypeptide on the surface of a T lymphocyte is disclosed. In one embodiment, the method comprises contacting a resting T lymphocyte with a modulator of P2Y10. In other embodiments, the modulator associates specifically with residues 171–191 of a P2Y10 polypeptide (SEQ ID NOs:3 and 4), and/or the modulator is an antibody, for example a monoclonal antibody, and/or is produced by the hybridoma strain identified as ATCC accession number PTA-3975.

Further, a method of upregulating transcription of P2Y10 mRNA in a resting T lymphocyte is disclosed. In one embodiment, the method comprises contacting a T lymphocyte with a modulator of P2Y10. In other embodiments, the modulator associates specifically with residues 171–191 of a P2Y10 polypeptide (SEQ ID NOs:3 and 4), and/or the modulator is an antibody, for example a monoclonal antibody, and/or is produced by the hybridoma strain identified as ATCC accession number PTA-3975.

Continuing, a method of inhibiting proliferation of an activated T lymphocyte is disclosed. In one embodiment, the method comprises contacting an activated T lymphocyte with a modulator of a P2Y10 polypeptide. In other embodiments, the modulator associates specifically with residues 171–191 of a P2Y10 polypeptide (SEQ ID NOs:3 and 4), and/or the modulator is an antibody, for example a monoclonal antibody, and/or is produced by the hybridoma strain identified as ATCC accession number PTA-3975.

A method of modulating an immune response is also disclosed. In one embodiment, the method comprises contacting a resting T lymphocyte with a modulator of P2Y10. In other embodiments, the modulator associates specifically with residues 171–191 of a P2Y10 polypeptide (SEQ ID NOs:3 and 4), and/or the modulator is an antibody, for example a monoclonal antibody, and/or is produced by the hybridoma strain identified as ATCC accession number PTA-3975.

Another method of treating an immune disease is disclosed. In one embodiment, the method comprises administering a modulator of a P2Y10 polypeptide, wherein the modulator has one or more properties selected from the group consisting of: (a) the ability to activate a resting T lymphocyte; (b) the ability to induce expression of a P2Y10 polypeptide on the surface of a resting T lymphocyte; (c) the ability to stimulate expression of mRNA encoding a P2Y10 polypeptide in a resting T lymphocyte; and (d) the ability to inhibit proliferation of an activated T lymphocyte. In other embodiments, the modulator associates specifically with residues 171–191 of a P2Y10 polypeptide (SEQ ID NOs:3 and 4), and/or the modulator is an antibody, for example a monoclonal antibody, and/or is produced by the hybridoma strain identified as ATCC accession number PTA-3975. The immune disease can be selected from the representative, but non-limiting, group consisting of rheumatoid arthritis, psoriatic arthritis, multiple sclerosis, juvenile diabetes, asthma, inflammatory bowel disease (such as Crohn's disease and ulcerative colitus), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia areata, autoimmune alopecia, autoimmune hypopituatarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, asthma, acute respiratory distress syndrome, Sezary's syndrome and vascular diseases which have an inflammatory and or a proliferatory component such as restenosis, stenosis and artherosclerosis. Inflammatory or immune associated diseases or disorders also includes, but is not limited to: endocrine disorders, rheumatic disorders, collagen diseases, dermatologic disease, allergic disease, opthalmic disease, respiratory disease, hematologic disease, gastrointestinal disease, inflammatory disease, autoimmune disease, congenital adrenal hyperplasia, nonsuppurative thyroiditis, hypercalcemia associated with cancer, psoriatic arthritis, rheumatoid arthritis, including juvenile rheumatoid arthritis, ankylosing spondylitis, acute and subacute bursitis, acute nonspecific tenosynovitis, acute gouty arthritis, post-traumatic osteoarthritis, synovitis of osteoarthritis, epicondylitis, systemic lupus erythematosus, acute rheumatic carditis, pemphigus, bullous dermatitis herpetiformis, severe erythema multiforme, exfoliative dermatitis, psoriasis, seborrheic dermatitis, seasonal or perennial allergic rhinitis, serum sickness, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, ulcerative colitis, regional enteritis, autoimmune vasculitis, multiple sclerosis, myasthenia gravis, anklyosing spondylitis, chronic obstructive pulmonary disease, solid organ transplant rejection, sepsis, and allergy.

Additionally, a pharmaceutical composition is disclosed. In one embodiment, the pharmaceutical composition comprises a modulator of a P2Y10 polypeptide that has one or more of the following properties: (a) the ability to activate a resting T lymphocyte; (b) the ability to induce surface expression of P2Y10 on a resting T lymphocyte; (c) the ability to stimulate P2Y10 mRNA expression in a resting T lymphocyte; and (d) the ability to inhibit proliferation of an activated T lymphocyte. In other embodiments, the modulator associates specifically with residues 171–191 of a P2Y10 polypeptide (SEQ ID NOs:3 and 4), and/or the modulator is an antibody, for example a monoclonal antibody, and/or is produced by the hybridoma strain identified as ATCC accession number PTA-3975.

A method of identifying a modulator of a P2Y10 polypeptide is also disclosed. In one embodiment, the method comprises (a) measuring the ability of a test molecule to bind to a P2Y10 polypeptide; and (b) measuring one or more of: (i) the ability of said test molecule to activate a resting T lymphocyte; (ii) the ability of said test molecule to induce surface expression of P2Y10 on a T lymphocyte; (iii) the ability of said test molecule to stimulate P2Y10 mRNA expression in a T lymphocyte; or (iv) the ability of said test molecule to inhibit proliferation of an activated T lymphocyte; whereby a test molecule is identified as a modulator if the test molecule binds to a P2Y10 polypeptide and exhibits one or more abilities selected from the group consisting of (i) to (iv). In other embodiments, the modulator associates specifically with residues 171–191 of a P2Y10 polypeptide (SEQ ID NOs:3 and 4), and/or the modulator is an antibody, for example a monoclonal antibody, and/or is produced by the hybridoma strain identified as ATCC accession number PTA-3975.

The present invention also relates to fusion proteins comprising P2Y10 or a modulator of P2Y10 and another protein. For example, a fusion protein of the present invention can comprise a P2Y10 protein and a Fc region from an immunoglobulin, such as IgG or a fusion comprising a P2Y10 modulator and an IgG. Such fusion proteins can impart or enhance a property of P2Y10 or a P2Y10 modulator, for example solubility, bioavailability or biotolerance.

Additionally, a hybridoma strain identified as ATCC accession number PTA-3975 is disclosed. The hybridoma can be employed to produce an antibody of the present invention.

Accordingly, it is an object of the present invention to provide a method of modulating T lymphocyte function. This object is achieved in whole or in part by the present invention.

An object of the invention having been stated hereinabove, other objects will be evident as the description proceeds, when taken in connection with the accompanying Drawings and Examples as described hereinbelow.

DETAILED DESCRIPTION OF THE INVENTION

Figure 1:
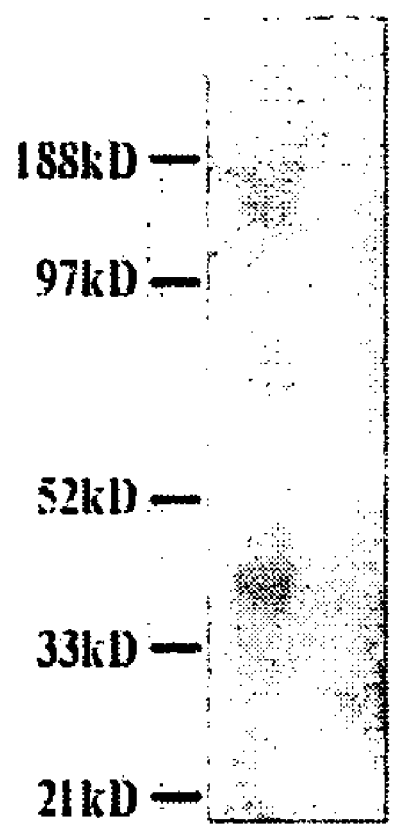
FIG. 1 is a photograph depicting a western blot of human peripheral blood B cells using anti-P2Y10 monoclonal antibody.

Since P2Y10 showed a lymphoid-restrictive expression pattern, in one aspect of the present invention, the role of P2Y10 in the proliferation of T cells when activated through the T cell receptor was investigated. In another aspect of the present invention a P2Y10-specific monoclonal antibody that modulates T cell function was generated and identified. The results of these and other experiments that form aspects of the present invention indicate that modulators of P2Y10 function might be employed in the diagnosis and/or treatment of a wide range of disorders of the immune system. These and other aspects of the present invention are described more fully below.

I. DEFINITIONS

| Amino Acid Abbreviations | | |
|---|---|---|
| Single-Letter Code | Three-Letter Code | Name |
| A | Ala | Alanine |
| V | Val | Valine |
| L | Leu | Leucine |
| I | Ile | Isoleucine |
| P | Pro | Proline |
| F | Phe | Phenylalanine |
| W | Trp | Tryptophan |
| M | Met | Methionine |
| G | Gly | Glycine |
| S | Ser | Serine |
| T | Thr | Threonine |
| C | Cys | Cysteine |
| Y | Tyr | Tyrosine |
| N | Asn | Asparagine |
| Q | Gln | Glutamine |
| D | Asp | Aspartic Acid |
| E | Glu | Glutamic Acid |
| K | Lys | Lysine |
| R | Arg | Arginine |
| H | His | Histidine |

| Functionally Equivalent Codons | | | |
|---|---|---|---|
| Amino Acid | | | Codons |
| Alanine | Ala | A | GCA GCC GCG GCU |
| Cysteine | Cys | C | UGC UGU |
| Aspartic Acid | Asp | D | GAC GAU |
| Glumatic Acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Methionine | Met | M | AUG |
| Asparagine | Asn | N | AAC AAU |
| Proline | Pro | P | CCA CCC CCG CCU |
| Glutamine | Gln | Q | CAA CAG |
| Threonine | Thr | T | ACA ACC ACG ACU |
| Valine | Val | V | GUA GUC GUG GUU |

-continued

| Tryptophan | Trp | W | UGG |
|---|---|---|---|
| Tyrosine | Tyr | Y | UAC UAU |
| Leucine | Leu | L | UUA UUG CUA CUC CUG CUU |
| Arginine | Arg | R | AGA AGG CGA CGC CGG CGU |
| Serine | Ser | S | ACG AGU UCA UCC UCG UCU |

All scientific and technical terms used in this application have meanings commonly used in the art unless otherwise specified. As used in this application, the following words or phrases have the meanings specified.

Following long-standing patent law convention, the terms "a" and "an" mean "one or more" when used in this application, including the claims.

As used herein, the term "about," when referring to a value or to an amount of mass, weight, time, volume, concentration or percentage is meant to encompass variations of ±20% or less (e.g., ±15%, ±10%, ±7%, ±5%, ±4%, ±3%, ±2%, ±1%, or ±0.1%) from the specified amount, as such variations are appropriate.

As used herein, the term "activated," when used in reference to a T lymphocyte means a T lymphocyte that is in a state of clonal expansion or clonal anergy or has been stimulated to proceed toward a state of clonal anergy or clonal expansion or is in a state in which it is capable of clonal expansion.

As used herein, the terms "agonist" and "activator" are synonymous and refer to an agent that initiates, supplements or potentiates the bioactivity of a functional P2Y10 gene or protein, or that supplements or potentiates the bioactivity of a naturally occurring or engineered functional P2Y10 gene or protein. An agonist can be a ligand. Further, an agonist can act by preventing an antagonist from acting on a given protein.

As used herein, the terms "amino acid," "amino acid residue" and "residue" are used interchangeably and mean any of the twenty naturally occurring amino acids. An amino acid is formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, abbreviations for amino acid residues are shown in tabular form presented herein above.

It is noted that the amino acid residue sequences represented herein by formulae have a left-to-right orientation, in the conventional direction of amino terminus to carboxy terminus. In addition, the phrases "amino acid" and "amino acid residue" are broadly defined to include modified and unusual amino acids.

Furthermore, it is noted that a dash at the beginning or end of an amino acid residue sequence indicates a peptide bond to a further sequence of one or more amino acid residues, a covalent bond to an amino-terminal group, such as $NH_2$, to an acetyl group or to a carboxy-terminal group, such as COOH.

As used herein, the term "antagonist" and "inhibitor" are synonymous and refer to an agent that decreases or inhibits the bioactivity of a functional P2Y10 gene or protein, or that decreases or inhibits the bioactivity of a naturally occurring or engineered P2Y10 gene or protein. An antagonist can be a ligand. Further, an antagonist can act by preventing an agonist from acting on a given protein.

As used herein, the term "antibody" means polyclonal, monoclonal, antibody fragments and antibody derivatives. The term encompasses antibodies prepared by recombinant techniques, such as chimeric or humanized antibodies, as well as single chain or bispecific antibodies. The term specifically encompasses antibodies that bind to an epitope, or a portion thereof, that is recognized by an antibody described in the present invention and/or is secreted by hybridoma strain PTA-3975.

As used herein, the terms "antigen" and "epitope," which are well understood in the art, mean all or a portion of a macromolecule that is specifically recognized by a component of the immune system, e.g., an antibody or a T-cell antigen receptor. An epitope is a region of an antigen. As used herein, the term "antigen" encompasses antigenic epitopes, e.g., fragments of an antigen that are antigenic epitopes.

As used herein, the terms "associate" and "bind," and grammatical derivations thereof, are used interchangeably and mean a condition of proximity between or amongst molecules, structural elements, chemical compounds or chemical entities. An association can be non-covalent (i.e., reversible), wherein the juxtaposition is energetically favored by hydrogen bonding or van der Waals or electrostatic interactions, or it can be covalent (i.e., irreversible). Thus in the present disclosure, when it is stated that a ligand "associates" with or "binds" to a protein, it is meant that the ligand interacts with the protein via covalent or non-covalent interactions. In one embodiment the ligand can be an antigen or epitope and the protein can be an antibody. In a related aspect, the term "associates specifically," and grammatical derivations thereof, means an interaction between a first moiety (e.g. a modulator) and a second moiety (e.g., a P2Y10 polypeptide or fragment thereof) that occurs preferentially to an interaction the first or second moiety and any other moieties present. For example, an antibody is presented with a variety of antigens, but only binds to a particular antigen. In this example, the antibody "specifically associates" with the particular antigen.

As used herein, the terms "bioactivity" and "biological activity" are used interchangeably and mean any observable effect flowing from interaction between a P2Y10 polypeptide and a ligand, including an antibody. Representative, but non-limiting, examples of biological activity in the context of the present invention include (a) the ability to activate a resting T lymphocyte, (b) the ability to induce expression of a P2Y10 polypeptide on the surface of a resting T lymphocyte, (c) the ability to stimulate expression of mRNA encoding a P2Y10 polypeptide in a resting T lymphocyte, and (d) the ability to inhibit proliferation of an activated T lymphocyte and modulating an immune response.

As used herein, the terms "chimeric protein" and "fusion protein" are used interchangeably and mean a fusion of a first molecule (e.g., a P2Y10 polypeptide or a modulator) with an amino acid sequence of second polypeptide molecule (e.g., an IgG Fc domain). In general, a chimeric or fusion protein of the present invention can be represented by the general formula X—P2Y10 polypeptide or modulator—Y, wherein modulator represents a modulator of the present invention, and X and Y are independently absent or represent the same or different molecules. In one embodiment, a chimeric protein comprises an IgG Fc domain fused to a modulator of the present invention. As discussed herein, a modulator of the present invention can be a small molecule, polypeptide or other structure. When the modulator is a polypeptide, such as a P2Y10 polypeptide, the fusion protein can be expressed from a single chimeric gene encoding the chimeric protein.

As used herein the term "complementary" means a nucleic acid sequence that is base paired, or is capable of base-pairing, according to the standard Watson-Crick complementarity rules. These rules generally hold that guanine pairs with cytosine (G:C) and adenine pairs with either thymine (A:T) in the case of DNA, or adenine pairs with uracil (A:U) in the case of RNA.

As used herein, the term "detecting" means confirming the presence of a target entity by observing the occurrence of a detectable signal, such as a radiologic, fluorescent, colorimetric, etc. signal that will appear exclusively in the presence of the target entity.

As used herein, the term "diagnosing" means determining the presence or absence of a condition in a subject. Although a subject is preferably a mammal, and more preferably a human, a subject can be any living entitiy, including individual cells, such as PBMCs. Further, in the context of the present invention, the term "condition" is used broadly and refers to any identifiable state, but preferably refers to a disease state, such as an immune disorder.

As used herein, the term "immune response" means a humoral and/or a cellular immune response. More particularly, a "humoral immune response" refers to an immune response mediated by antibody molecules, while a "cellular immune response" is one mediated by T-lymphocytes and/or other white blood cells.

Continuing, an immune response can be one that stimulates the production of cytotoxic T lymphocytes (CTLs), and/or the production or activation of helper T-cells and/or the elicitation of an antibody-mediated immune response. Hence, an immune response can include one or more of the following effects: the production of antibodies by, e.g., but not limited to B-cells; and/or the activation of suppressor T-cells and/or activation of γδ T-cells directed specifically to an antigen or antigens present in the composition or vaccine of interest.

As used herein, the terms, "increasing," "inducing," and "enhancing," and grammatical derivations thereof, are used interchangeably herein with reference to an immune response (e.g., a CTL response or a humoral response), and refer to any increase in an immune response over background; the terms include inducing an immune response over an absence of a measurable immune response, or increasing immune response over a previously measurable immune response.

As used herein, the term "inhibit" and grammatical derivations thereof, means to decrease, limit, or block an action or function. For example, the term can be applied to T lymphocyte activation, in which usage it means to decrease, limit or block activation of a T lymphocyte.

As used herein, the terms "isolated" and "purified" are used interchangeably and refer to material (e.g., a nucleic acid or a polypeptide) removed from its original environment (e.g., the natural environment, if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide and/or protein sequences of the present invention; such sequences are excluded from the scope of the present invention.

As used herein, the term "ligand" means any molecule that is known or suspected to associate with another molecule. The term "ligand" encompasses inhibitors, activators, agonists, antagonists, natural substrates and analogs of natural substrates. A ligand can comprise, for example, a nucleic acid sequence, an amino acid sequence (e.g. a peptide and/or polypeptide) or a small molecule.

As used herein the term "modulate," and grammatical derivations thereof, refer to an increase, decrease, or other alteration of any and/or all chemical and/or biological activities or properties mediated by a given DNA sequence, RNA sequence, polypeptide, peptide or molecule. The definition of "modulator" as used herein encompasses agonists and/or antagonists of a particular activity or protein. The term "modulate" therefore refers to both upregulation (i.e., activation or stimulation) and downregulation (i.e. inhibition or suppression) of a response by any mode of action. In one embodiment, a modulator modulates protein (e.g., P2Y10) activity. In another embodiment, a modulator modulates transcription of a gene (e.g. a P2Y10 gene).

As used herein, the terms "organism", "subject" and "patient" are used interchangeably and mean any organism referenced herein, including prokaryotes, though the terms preferably refer to eukaryotic organisms, notably mammals (e.g., mice, rats, dogs and pigs), but most preferably to humans. The methods of the present invention are particularly useful in the treatment and diagnosis of warm-blooded vertebrates.

As used herein, the terms "P2Y10 gene" and "recombinant P2Y10 gene" mean a nucleic acid molecule comprising an open reading frame encoding a P2Y10 polypeptide of the present invention, including both exon and (optionally) intron sequences.

As used herein, the terms "P2Y10 gene product", "P2Y10 protein", "P2Y10 polypeptide", "P2Y10 polypeptide gene product" and "P2Y10 peptide" are used interchangeably and mean peptides having amino acid sequences which are substantially identical to native amino acid sequences from an organism of interest and which are biologically active in that they comprise all or a part of the amino acid sequence of a P2Y10 polypeptide, or cross-react with antibodies raised against a P2Y10 polypeptide. Such biological activity can include immunogenicity. In one embodiment, a "P2Y10 gene product", "P2Y10 protein", "P2Y10 polypeptide", "P2Y10 polypeptide gene product" or "P2Y10 peptide" is encoded by the sequence of GenBank Accession Number AF000545 (SEQ ID NO:1) and has the amino acid sequence of SEQ ID NO:2.

As used herein, the terms "P2Y10 gene product", "P2Y10 protein", "P2Y10 polypeptide", "P2Y10 polypeptide gene product" and "P2Y10 peptide" also include analogs of a P2Y10 polypeptide. By "analog" is intended that a DNA or peptide sequence can contain alterations relative to the sequences disclosed herein, yet retain all or some of the biological activity of those sequences. Analogs can be derived from genomic nucleotide sequences as are disclosed herein or from other organisms, or can be created synthetically. Those skilled in the art will appreciate that other analogs, as yet undisclosed or undiscovered, can be used to design and/or construct P2Y10 analogs. There is no need for a "P2Y10 gene product", "P2Y10 protein", "P2Y10 polypeptide", or "P2Y10 peptide" to comprise all or substantially all of the amino acid sequence of a full length P2Y10 polypeptide gene product.

The terms a "P2Y10 gene product", "P2Y10 protein", "P2Y10 polypeptide", and "P2Y10 peptide" encompass sequences comprising one or more conservative substitutions in the P2Y10 amino acid sequence of SEQ ID NO:2. The substititution can be naturally occurring or introduced by man. In a conservative substitution, the replacement group will have approximately the same size, shape, hydrophobicity and charge as the original group. A table disclosing some representative, but non-limiting properties that can be used as a guide when identifying or generating a conservative mutation follows:

Representative Conservative Amino Acid Substitutions

| Amino Acid Property | Amino Acid |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative amino acid substitutions can be taken from the table below.

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, .beta.-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline or | P | D-Pro, L-1-thioazolidine-4-carboxylic acid, D-L-1-oxazolidine-4-carboxylic acid |

-continued

| For Amino Acid | Code | Replace with any of: |
|---|---|---|
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

The terms a "P2Y10 gene product", "P2Y10 protein", "P2Y10 polypeptide", and "P2Y10 peptide" encompass natural variants of a P2Y10 polypeptide (e.g. SEQ ID NO:2). As used herein, the term "natural variant" means a form of P2Y10 that comprises more or fewer amino acids than the sequence of SEQ ID NO:2, however in a natural variant the addition or deletion of amino acids from the sequence of SEQ ID NO:2 is a natural event and occurs in vivo without intervention by man. For example a P2Y10 natural variant is the result of a naturally occurring splicing event that occurs in the process of transcribing a P2Y10 polypeptide-encoding sequence (e.g., SEQ ID NO:1). Thus the terms encompass allelic variants, genetically altered versions of the gene, etc.

Shorter or longer sequences are anticipated to be of use in the present invention; shorter sequences are herein referred to as "segments". In some embodiments, a shorter or longer sequence derived from a P2Y10 polypeptide retains the biological activity of a full length P2Y10 polypeptide, namely (a) the ability to activate a resting T lymphocyte, (b) the ability to induce expression of a P2Y10 polypeptide on the surface of a resting T lymphocyte, (c) the ability to stimulate expression of mRNA encoding a P2Y10 polypeptide in a resting T lymphocyte, and (d) the ability to inhibit proliferation of an activated T lymphocyte and modulating an immune response.

Thus, the terms "P2Y10 gene product", "P2Y10 protein", "P2Y10 polypeptide", and "P2Y10 peptide" also include fusion, chimeric or recombinant P2Y10 polypeptides and proteins comprising sequences of the present invention. Methods of preparing such proteins are disclosed herein and are known in the art.

As used herein, the terms "protein", "polypeptide" and "peptide" are used interchangeably and mean any polymer comprising any of the 20 protein amino acids, regardless of its size. Although "protein" is often used in reference to relatively large polypeptides, and "peptide" is often used in reference to small polypeptides, usage of these terms in the art overlaps and varies. Therefore, term "polypeptide" as used herein refers to peptides, polypeptides and proteins, unless otherwise noted. Further, the terms "protein", "polypeptide" and "peptide" are used interchangeably herein.

Thus, a polypeptide of the present invention can comprise amino acids joined to each other by peptide bonds or modified peptide bonds, i.e., peptide isosteres, and can contain amino acids other than the 20 gene-encoded amino acids. A polypeptide can be modified by either natural processes, such as by posttranslational processing, or by chemical modification techniques which are known in the art. Such modifications will be known to those of ordinary skill in the art. Modifications can occur anywhere in a polypeptide, including the peptide backbone, the amino acid side-chains and the amino or carboxyl termini. The same type of modification can be present in the same or varying degrees at several sites in a given polypeptide.

Also, a given polypeptide can contain many types of modifications. A polypeptide can be branched, for example, as a result of ubiquitination, or a polypeptide can be cyclic, with or without branching. Cyclic, branched, and branched cyclic polypeptides can result from posttranslation natural processes or can be made by synthetic methods. Representative modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination (see, e.g., Creighton, *Proteins—Structure And Molecular Properties*, 2nd ed., W. H. Freeman and Company, New York, N.Y., USA (1993); *Posttranslational Covalent Modification Of Proteins*, (Johnson, ed.), Academic Press, New York, N.Y., USA, pp. 1–12 (1983); Seifter et al., (1990) *Method Enzymol.* 182:626–646; Rattan et al., (1992) *Ann. N.Y. Acad. Sci.* 663:48–62, incorporated herein by reference).

As used herein, the term "polypeptide fragment" means an amino acid sequence that is at least one amino acid shorter than a reference sequence, but retains the order of amino acids in the reference sequence. For example, a "polypeptide fragment" of a P2Y10 polypeptide means an amino acid sequence that is at least 338 amino acids in length (one residue less than the 339 residues shown in SEQ ID NO:2). In another example, a polypeptide fragment of a P2Y10 polypeptide comprises residues 171–191 (SEQ ID NOs:3 and 4) of a P2Y10 polypeptide (SEQ ID NO:2).

As used herein, the term "resting" when used in reference to a T lymphocyte means a T lymphocyte that is not in a state of clonal expansion or clonal anergy or that has not been stimulated to proceed toward a state of clonal expansion or clonal anergy or that is in a state in which it is not capable of clonal expansion.

As used herein, the term "small molecule" means any molecule having a molecular weight of 5000 Daltons or less.

As used herein, the term "substantially identical" means at least 70% sequence identity between two amino acid sequences. Sequence identity is calculated based on a reference sequence, which can be a subset of a larger sequence. A reference sequence will usually be at least about 6 amino acids long or more usually at least about 10 amino acids long, and can extend to the complete sequence that is being compared. Algorithms for sequence analysis are known in the art, such as BLAST, described in Altschul et al., (1990) *J. Mol. Biol.* 215: 403–10.

The term "similarity" is contrasted with the term "identity". Similarity is defined as above; "identity", however, means an amino acid sequence having the same amino acid at the same relative position in a given family member of a gene family. Homology and similarity are generally viewed as broader terms than the term identity. Biochemically similar amino acids, for example leucine/isoleucine or glutamate/aspartate, can be present at the same position—these are not identical per se, but are biochemically "similar." As disclosed herein, these are referred to as conservative differences or conservative substitutions. This differs from a conservative mutation at the DNA level, which changes the nucleotide sequence without making a change in the encoded amino acid, e.g. TCC to TCA, both of which encode serine.

Polypeptides that are substantially identical to a P2Y10 polypeptide (SEQ ID NO:2) can have between about 70% and 80%, preferably between about 81% to about 90% or even more preferably between about 91% and 99% sequence identity with the corresponding sequence of the native P2Y10 protein. Sequences having lesser degrees of identity but comparable biological activity are considered to be equivalents.

As used herein, the term "T lymphocyte" means any immune system cell that originates in the thymus, including cytotoxic cells, helper cell and suppressor cells in general, and CD4+ and CD8+ cells in particular. Such cells are normally, but not necessarily, capable of producing one or more cytokines.

As used herein, the term "vector" means a replicon, such as plasmid, phage or cosmid, to which another DNA segment may be attached so as to bring about the replication of the attached segment.

II. Description of Tables

Table 1 is a table showing P2Y10 surface expression on stimulated T cells as measured by FACS.

Table 2 is a table showing the effect of anti-P2Y10 on T cell proliferation.

Table 3 is a table showing the effect of antigenic peptide on anti-P2Y10 inhibition of anti-CD3-induced T cell proliferation.

III. Antibodies of the Present Invention

In one aspect, the present invention relate to antibodies that associates specifically with a polypeptide, polypeptide fragment, or variant of a P2Y10 polypeptide, and/or a P2Y10 epitope (as can be determined by immunoassays known in the art for assaying specific antibody-antigen binding). Antibodies of the present invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the present invention), and epitope-binding fragments of any of the polypeptides and peptides disclosed herein.

The antibodies of the present invention can be monospecific, bispecific, trispecific or of greater multispecificity. Multispecific antibodies can be specific for different epitopes of a P2Y10 polypeptide of the present invention or can be specific for both a P2Y10 polypeptide of the present invention as well as for a heterologous epitope, such as a heterologous polypeptide or solid support material. See, e.g., PCT Publications WO 93/17715; WO 92/08802; WO 91/00360; WO 92/05793; U.S. Pat. Nos. 4,474,893; 4,714,681; 4,925,648; 5,573,920; 5,601,819; Kostelny et al., (1992) *J. Immunol.* 148:1547–1553; Tutt et al., (1991) *J. Immunol.* 147:60–69.

Antibodies of the present invention can be described or specified in terms of an epitope(s) or portion(s) of a polypeptide that a given antibody recognizes or specifically binds (e.g., residues 171–191 of a P2Y10 polypeptide; SEQ ID NOs:3 and 4). The epitope(s) or polypeptide portion(s) can be specified as described herein, e.g., by N-terminal and C-terminal positions, by size in contiguous amino acid residues, or listed in the Tables, Figures and/or Sequence Listing. Therefore, the present invention includes antibodies that specifically bind P2Y10 peptides and polypeptides.

Antibodies of the present invention can also be described in terms of their properties, such as their effect on the activation of a resting T lymphocyte and the inhibition of the proliferation of an activated T lymphocyte. More particularly, an antibody of the present invention has one or more of the following properties: (a) the ability to activate a resting T lymphocyte; (b) the ability to induce surface expression of P2Y10 on a resting T lymphocyte; (c) the ability to stimulate P2Y10 mRNA expression in a resting T lymphocyte; and (d) the ability to inhibit proliferation of an activated T lymphocyte. These properties are described further throughout the present disclosure.

Antibodies of the present invention can also be described or specified in terms of their cross-reactivity. Antibodies that do not bind any other analog, ortholog, or homologue of a P2Y10 polypeptide of the present invention are included in the scope of the present invention. Antibodies that bind a P2Y10 polypeptide (e.g., sSEQ ID NO:2) with at least 95%, at least 90%, at least 85%, at least 80%, at least 75%, at least 70%, at least 65%, at least 60%, at least 55%, and at least 50% identity (as calculated using methods known in the art and/or as described herein) or to a P2Y10 polypeptide or fragment (e.g., SEQ ID NOs:3 and 4) are also encompassed by the present invention. In specific embodiments, antibodies of the present invention cross-react with murine, rat and/or rabbit homologues of human proteins and the corresponding epitopes thereof.

In a specific embodiment, the above-described cross-reactivity is with respect to any single specific antigenic or immunogenic P2Y10 polypeptide, or combination(s) of 2, 3, 4, 5, or more of the specific antigenic and/or immunogenic P2Y10 polypeptides disclosed herein. Antibodies of the present invention can also be described or specified in terms of their binding affinity to a P2Y10 polypeptide of the present invention. Representative binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $1\times10^{-5}$ M, $5\times10^{-6}$ M, $1\times10^{-6}$ M, $5\times10^{-7}$ M, $1\times10^{-7}$ M, $5\times10^{-8}$ M, $1\times10^{-8}$ M, $5\times10^{-9}$ M, $1\times10^{-9}$ M, $5\times10^{-10}$ M, $1\times10^{-10}$ M, $5\times10^{-11}$ M, $1\times10^{-11}$ M, $5\times10^{-12}$ M, $10^{-12}$ M, $5\times10^{-13}$ M, $1\times10^{-13}$ M, $5\times10^{-14}$ M, $1\times10^{-14}$ M, $5\times10^{-15}$ M, or $1\times10^{-15}$ M.

The present invention also provides antibodies that competitively inhibit binding of a ligand to an epitope of the present invention as determined by any method known in the art for determining competitive binding, for example, the immunoassays described herein. In representative embodiments, the antibody competitively inhibits binding to the epitope by at least 95%, at least 90%, at least 85%, at least 80%, at least 75%, at least 70%, at least 60%, or at least 50%.

An antibody of the present invention includes derivatives that are modified, i.e., by the covalent attachment of any type of molecule to the antibody such that covalent attachment does not prevent the antibody from generating an anti-idiotypic response. For example, but not by way of limitation, an antibody derivative includes antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc. Additionally, a derivative can contain one or more non-classical amino acids.

An antibody of the present invention can exert a stimulating or blocking effect on an antigen. More specifically, by binding an antigen, an antibody of the present invention can block other molecules from binding to or associating with the antigen. The blocking can be a steric consequence of binding the antigen. The blocking effect can have the overall effect of modulating one or more cellular processes by preventing association of other molecules with the antigen or via the binding event itself. Alternatively, the binding event can have a stimulating effect on one or more cellular processes as a result of the binding event itself or by making interactions between the antigen and another molecule more feasible and/or more productive that is normally the case.

III.A. Polyclonal Antibodies

The antibodies of the present invention can comprise polyclonal antibodies. Methods of preparing polyclonal antibodies are known to the skilled artisan (Harlow et al., *Antibodies: A Laboratory Manual*, $2^{nd}$ ed., Cold Spring Harbor Laboratory Press, Cold Spring Harbor, N.Y., USA (1988)). In one method, a preparation of a P2Y10 polypeptide is prepared and purified to render it substantially free of natural contaminants. Such a preparation is then introduced into an animal in order to produce polyclonal antisera of greater specific activity. For example, a P2Y10 polypeptide of the present invention can be administered to various host animals including, but not limited to, rabbits, mice, rats, etc. to induce the production of sera containing polyclonal antibodies specific for the antigen. The administration of a P2Y10 polypeptide of the present invention can entail one or more injections of an immunizing agent and, if desired, an adjuvant. Various adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are known to those or ordinary skill in the art. For the purposes of the present invention, "immunizing agent" is defined as a P2Y10 polypeptide of the present invention, including fragments, variants, and/or derivatives thereof, in addition to fusions with heterologous polypeptides and other forms of the polypeptides described herein.

In some embodiments, the immunizing agent and/or adjuvant is injected into the subject (for example a mammal) by multiple subcutaneous or intraperitoneal injections, though they may also be administered intramuscularly, and/or through IV injection. The immunizing agent can include polypeptides of the present invention or a fusion protein or variants thereof. Depending on the nature of the polypeptides (i.e., percent hydrophobicity, percent hydrophilicity, stability, net charge, isoelectric point etc.), it might be useful to conjugate the immunizing agent to a protein known to be immunogenic in the mammal being immunized. Such a conjugation can include either chemical conjugation by derivitizing active chemical functional groups to both the polypeptide of the present invention and the immunogenic protein such that a covalent bond is formed, or through fusion-protein based methodology, or other methods known to those of ordinary skill in the art. Examples of such immunogenic proteins include, but are not limited to keyhole limpet hemocyanin (KLH), serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as bacille Calmette-Guerin (BCG) and *Corynebacterium parvum*. Additional examples of adjuvants that can be employed include the MPL-TDM adjuvant (monophosphoryl lipid A, synthetic trehalose dicorynomycolate). A suitable immunization protocol can be selected by one of ordinary skill in the art upon consideration of the present disclosure.

III.B. Monoclonal Antibodies

The antibodies of the present invention can comprise monoclonal antibodies. Monoclonal antibodies can be prepared using known hybridoma methods, as described herein and as is known to those of ordinary skill in the art (see, e.g., Köhler & Milstein, (1975) *Nature* 256:495; U.S. Pat. No. 4,376,110, Harlow et al., *Antibodies: A Laboratory Manual*, $2^{nd}$ ed., Cold Spring Harbor Laboratory Press, Cold Spring Harbor, N.Y., USA (1988); Hammerling et al., *Monoclonal Antibodies and T-Cell Hybridomas*, Elsevier, New York, N.Y., USA, (1981) pp. 563–681; Köhler et al., (1976) *Eur. J. Immunol.* 6:511; Köhler et al., (1976) *Eur. J. Immunol.* 6:292). Indeed hybridoma strain PTA-3975, which produces an antibody of the present invention, has been prepared and itself forms an aspect of the present invention.

Other examples of methods that can be employed for producing monoclonal antibodies include, but are not limited to, the human B-cell hybridoma technique (Kosbor et al., (1983) *Immunology Today* 4:72; Cole et al., (1983) *Proc. Natl. Acad. Sci. USA* 80:2026–2030), and the EBV-hybridoma technique (Cole et al., *Monoclonal Antibodies And Cancer Therapy*, Alan R. Liss, Inc., New York, N.Y., USA (1985) pp. 77–96). Such antibodies can be of any immunoglobulin class including IgG, IgM, IgE, IgA, IgD and any subclass thereof. A hybridoma producing a monoclonal antibody of the present invention can be cultivated in vitro or in vivo. Production of high titers of monoclonal antibodies in vivo makes this a desirable method of production in some situations.

Methods for producing and screening for specific antibodies using hybridoma technology are routine and well known in the art and are discussed below and elsewhere herein. In a non-limiting example, mice can be immunized with a P2Y10 polypeptide, or fragment thereof (e.g., residues 171–191 of a P2Y10 polypeptide; SEQ ID NOs:3 and 4), of the present invention or a cell expressing such a polypeptide or fragment. Once an immune response is detected, e.g., antibodies specific for the antigen are detected in the mouse serum, the mouse spleen is harvested and splenocytes isolated. The splenocytes are then fused by known techniques to any suitable myeloma cells, for example cells from a cell line available from the ATCC. Hybridomas are selected and cloned by limited dilution. The hybridoma clones are then assayed by methods known in the art for cells that secrete antibodies capable of binding a polypeptide of the present invention. Ascites fluid, which generally contains high levels of antibodies, can be generated by immunizing mice with positive hybridoma clones.

Accordingly, in one aspect, the present invention provides a method of generating a monoclonal antibody that specifically associates with a P2Y10 polypeptide, or a fragment thereof, as well as antibodies produced by the method, comprising: (i) culturing a hybridoma cell secreting an antibody of the present invention (e.g., an antibody that specifically associates with a P2Y10 polypeptide or a fragment thereof), optionally wherein the hybridoma is generated by fusing splenocytes isolated from a mouse immunized with an antigen of the present invention (e.g. a P2Y10 polypeptide or a peptide comprising residues 171–191 of P2Y10; SEQ ID NOs:3 and 4) with myeloma cells; and (ii) screening the hybridomas resulting from the fusion for hybridoma clones that secrete an antibody that specifically associates with a P2Y10 polypeptide or a fragment thereof.

A variety of methods exist in the art for the production of monoclonal antibodies and thus, the present invention is not limited solely to their production in hydridomas. For example, monoclonal antibodies of the present invention can be made by employing recombinant DNA methods, such as those described in U.S. Pat. No. 4,816,567. In this context, the term "monoclonal antibody" refers to an antibody derived from a single eukaryotic, phage, or prokaryotic clone. DNA encoding a monoclonal antibody of the present invention can be readily isolated and sequenced using conventional procedures (e.g., by using oligonucleotide probes that are capable of binding specifically to genes encoding the heavy and light chains of murine antibodies, or such chains from human, humanized, or other sources). The hydridoma cells of the present invention (e.g. PTA-3975) can serve as a source of such DNA. Once isolated, the DNA can be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, (1985) *Science* 229:1202) or by covalently joining to the immunoglobulin coding sequence all or part of the coding sequence for a non-immunoglobulin polypeptide. Such a non-immunoglobulin polypeptide can be substituted for the constant domains of an antibody of the present invention, or can be substituted for the variable domains of one antigen-combining site of an antibody of the present invention to create a chimeric bivalent antibody.

Monoclonal antibodies can be prepared using a wide variety of techniques known in the art including the use of a hybridoma and recombinantly, as described above, as well as phage display technologies, or a combination thereof. For example, monoclonal antibodies can be produced using hybridoma techniques, including those known in the art and taught, for example, in Harlow et al., *Antibodies: A Laboratory Manual*, $2^{nd}$ ed., Cold Spring Harbor Laboratory Press, Cold Spring Harbor, N.Y., USA (1988); Hammerling et al., in: *Monoclonal Antibodies and T-Cell Hybridomas*, Elsevier, New York, N.Y., USA, (1981) pp. 563–681. The term "monoclonal antibody" as used herein is not limited to antibodies produced through hybridoma technology. Rather, the term "monoclonal antibody" broadly refers to an antibody that is derived from a single clone, including any eukaryotic, prokaryotic, or phage clone, and not the method by which it is produced.

Antibody fragments that recognize specific epitopes (e.g., residues 171–191 of a P2Y10 polypeptide; SEQ ID NOs:3 and 4) can be generated by known techniques. For example, Fab and F(ab')$_2$ fragments of the present invention can be produced by proteolytic cleavage of immunoglobulin molecules, using enzymes such as papain (to produce Fab fragments) or pepsin (to produce F(ab')$_2$ fragments). F(ab')$_2$ fragments contain a variable region, a light chain constant region and a CH1 domain of the heavy chain.

III.C. Human and Humanized Antibodies

Humanized antibodies form an aspect of the present invention (e.g., a humanized anti-P2Y10 antibody). Humanized antibodies are antibody molecules from non-human species that bind a desired antigen and comprising one or more complementarity determining regions (CDRs) from the non-human species as well as a framework region from a human immunoglobulin molecule. Often, framework residues in the human framework regions can be substituted with the corresponding residue from a CDR donor antibody to alter, and preferably improve, antigen binding. These framework substitutions can be identified by methods known in the art, e.g., by modeling of the interactions of the CDR and framework residues to identify framework residues important for antigen binding and sequence comparison to identify unusual framework residues at particular positions (see, e.g., U.S. Pat. No. 5,585,089; Riechmann et al., (1988) *Nature* 332:323). Antibodies can be humanized using a variety of techniques known in the art including, for example, CDR-grafting (EP 239,400; PCT Publication WO 91/09967; U.S. Pat. Nos. 5,225,539; 5,530,101; and 5,585,089), veneering or resurfacing (EP 592,106; EP 519,596; Padlan, (1991) *Molecular Immunology* 28(4/5):489–498; Studnicka et al., (1994) *Protein Engineering* 7(6):805–814; Roguska et al., (1994) *Proc. Natl. Acad. Sci. U.S.A.* 91:969–973), and chain shuffling (U.S. Pat. No. 5,565,332), each of which is incorporated herein by reference.

Generally, a humanized antibody has one or more amino acid residues introduced into it from a source that is non-human. These non-human amino acid residues are often referred to as "import" residues, which are typically taken from an "import" variable domain. Humanization can be essentially performed following known methods (Jones et al., (1986) *Nature* 321:522–525 (1986); Reichmann et al., (1988) *Nature* 332:323–327; Verhoeyen et al., (1988) *Science* 239:1534–1536) by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are sometimes human antibodies in which some CDR residues and possible some FR residues are substituted from analogous sites in rodent antibodies.

In general, a humanized antibody comprises substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody can also comprise at least a portion of an immunoglobulin constant region (Fc), typically that of a human immunoglobulin (see Jones et al., (1986) *Nature* 321:522–525; Riechmann et al., (1988) *Nature* 332:323–329 and Presta, (1992) *Curr. Opin. Struct. Biol.* 2:593–596).

Completely human antibodies are particularly desirable for therapeutic treatment of human subjects. Human antibodies can be made by a variety of methods known in the art including phage display methods described herein using antibody libraries derived from human immunoglobulin sequences. See also, U.S. Pat. Nos. 4,444,887 and 4,716,111; and PCT Publications WO 98/46645, WO 98/50433, WO 98/24893, WO 98/16654, WO 96/34096, WO 96/33735, and WO 91/10741. Other techniques are also available for the preparation of human monoclonal antibodies (Cole et al., *Monoclonal Antibodies and Cancer Therapy*, Alan R. Liss, New York, N.Y., USA (1985); and Boerner et al., (1991) *J. Immunol.* 147(1):86–95).

Human antibodies can also be produced using transgenic mice that are incapable of expressing functional endogenous immunoglobulins, but can express human immunoglobulin genes. For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring, which express human antibodies. The transgenic mice are immunized in the normal fashion with a selected antigen, e.g., all or a portion of a polypeptide of the present invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg & Huszar, (1995) *Int. Rev. Immunol.* 13:65–93. See also PCT Publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, all of which are incorporated herein by reference. In addition, companies such as Abgenix, Inc. (Fremont, Calif., USA), Genpharm (San Jose, Calif., USA), and Medarex, Inc. (Princeton, N.J., USA) can be engaged to provide human antibodies directed against a selected antigen using technology similar to that described herein.

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., (1992) *Biotechnol.* 10:779–783; Lonberg et al., (1994) *Nature* 368:856–859; Fishwild et al., (1996) *Nature Biotechnol.* 14:845–51; Neuberger, (1996) *Nature Biotechnol.* 14:826; Lonberg & Huszer, (1995) *Intern. Rev. Immunol.* 13:65–93.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., (1988) *Bio/technology* 12:899–903).

III.D. Monospecific/Monovalent Antibodies

The antibodies of the present invention can be monovalent antibodies. Methods for preparing monovalent antibodies are known in the art. For example, one method involves recombinant expression of immunoglobulin light chain and modified heavy chain. The heavy chain is generally truncated at a point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

III.E. Bispecific/Bivalent Antibodies

The antibodies of the present invention can also be bispecific antibodies. Bispecific antibodies are monoclonal antibodies (e.g., human or humanized monoclonal antibodies) that have binding specificities for at least two different antigens. In a bispecific antibody of the present invention, one of the binding specificities can be directed a P2Y10 polypeptide of the present invention, the other can be for any other antigen (e.g., a T lymphocyte-surface protein, receptor, receptor subunit, tissue-specific antigen, virally derived protein, virally encoded envelope protein, bacterially derived protein, interleukin, etc.).

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein & Cuello, (1983) *Nature* 305:537–539). Because of the random assortment of immunoglobulin heavy and light chains, these hybridomas (quadromas) produce a potential mixture of ten different antibody molecules, of which only one has the correct bispecific structure. The purification of the correct molecule can be accomplished by affinity chromatography steps. Similar procedures are disclosed in PCT Publication WO 93/08829 and in Traunecker et al., (1991) *EMBO J.* 10:3655–3659.

Antibody variable domains with the desired binding specificities (antibody-antigen combining sites) can be fused to immunoglobulin constant domain sequences. The fusion can be with an immunoglobulin heavy-chain constant domain, comprising at least part of the hinge, CH2, and CH3 regions. It is somteimes desirable to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details on generating bispecific antibodies see, e.g., Suresh et al., (1986) *Meth. Enzymol.* 121:210.

III.F. Anti-Idiotype Antibodies

Antibodies to a P2Y10 polypeptide, or fragment thereof (e.g., SEQ ID NOs:3 and 4), can, in turn, be utilized to generate anti-idiotype antibodies that "mimic" a P2Y10 polypeptide or P2Y10 polypeptide fragment using techniques known to those skilled in the art (see, e.g., Greenspan & Bona, (1989) *FASEB J.* 7(5):437–444; and Nissinoff, (1991) *J. Immunol.* 147(8):2429–2438). For example, antibodies that specifically associate with, and inhibit or facilitate, an association of a P2Y10 polypeptide, or a fragment thereof, with a ligand, can be used to generate anti-idiotypes that "mimic" a P2Y10 binding domain and, as a consequence, bind to and inhibit or augment the biological effect of the ligand binding event. Neutralizing anti-idiotypes or Fab fragments of such anti-idiotypes can be used in therapeutic regimens to neutralize a P2Y10 polypeptide ligand. For example, such anti-idiotypic antibodies can be used to bind a P2Y10 polypeptide, or fragment thereof, of the present invention and/or to bind its ligands, and thereby block the polypeptide and/or ligand's biological activity.

Such anti-idiotypic antibodies capable of binding a P2Y10 polypeptide can be produced in a two-step procedure. Such a method makes use of the fact that antibodies are themselves antigens, and therefore, it is possible to obtain an antibody that binds to a second antibody. In accordance with this method, protein-specific antibodies (e.g. P2Y10-specific antibodies) can be used to immunize an animal, for example a mouse. The splenocytes of such an animal are then used to produce hybridoma cells, and the hybridoma cells are screened to identify clones that produce an antibody whose ability to bind to the protein-specific antibody can be blocked by the polypeptide itself. Such antibodies comprise anti-idiotypic antibodies to the protein-specific antibody and can be used to immunize an animal to induce formation of further protein-specific antibodies.

III.G. Heteroconjugate Antibodies

Heteroconjugate antibodies are also contemplated by the present invention. Heteroconjugate antibodies comprise two covalently joined antibodies. Such antibodies have, for example, been proposed for targeting immune system cells to unwanted cells (U.S. Pat. No. 4,676,980), and for the treatment of HIV infection (PCT Publications WO 91/00360; WO 92/20373; and EP03089). It is contemplated that the antibodies can be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

IV. Polynucleotides Encoding Antibodies

The present invention further encompasses polynucleotides comprising a nucleotide sequence encoding an antibody of the present invention and fragments thereof. The present invention also encompasses polynucleotides that hybridize under stringent or lower stringency hybridization conditions to polynucleotides that encode an antibody of the present invention, for example an antibody that specifically binds to a P2Y10 polypeptide or an antibody that binds to a fragment of a P2Y10 polypeptide comprising the amino acid sequence of residues 171–191 of a P2Y10 polypeptide (i.e., SEQ ID NOs:3 and 4).

The polynucleotides can be obtained, and the nucleotide sequence of the polynucleotides determined, by any method known to those of ordinary skill in the art. For example, if the nucleotide sequence encoding an antibody is known, a polynucleotide encoding the antibody can be assembled from chemically synthesized oligonucleotides (e.g., as described in Kutmeier et al., (1994) *BioTechniques* 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody of the present invention can be generated from a nucleic acid derived from a suitable source. If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library, or a cDNA library generated from a nucleic acid, for example poly A+ RNA, isolated from any tissue or cells expressing the antibody, such as hybridoma cells selected to express an antibody of the present invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method known in the art.

Once the nucleotide sequence and corresponding amino acid sequence of the antibody is determined, the nucleotide sequence of the antibody can be manipulated using methods known in the art for the manipulation of nucleotide sequences, e.g., recombinant DNA techniques, site directed mutagenesis, PCR, etc. (see, for example, the techniques described in Sambrook et al., *Molecular Cloning: A Laboratory Manual*, ($3^{rd}$ ed.) Cold Spring Harbor Laboratory Press, Cold Spring Harbor, N.Y., USA (2001), and *Current Protocols in Molecular Biology*, (Ausubel et al., eds.), Greene Publishing Associates and Wiley-Interscience, New York, N.Y., USA (2002), and discussion presented herein below), to generate antibodies having a different amino acid sequence, for example to create amino acid substitutions, deletions, and/or insertions.

In a specific embodiment, an amino acid sequence of the heavy and/or light chain variable domains can be inspected to identify the sequences of the complementarity determining regions (CDRs) by methods that are known in the art, e.g., by comparison to known amino acid sequences of other heavy and light chain variable regions to determine a region(s) of sequence hypervariability. Using routine recombinant DNA techniques, one or more of the CDRs can be inserted within framework regions, e.g., into human framework regions to humanize a non-human antibody, as described herein. The framework regions can be naturally occurring or consensus framework regions, (e.g., human framework regions (see, e.g., Chothia et al., (1998) *J. Mol. Biol.* 278:457–479 for a listing of representative human framework regions). A polynucleotide generated by the combination of the framework regions and CDRs can encode an antibody that specifically binds a P2Y10 polypeptide or fragment thereof. As discussed herein, one or more amino acid substitutions can be made within the framework regions, and the amino acid substitutions improve binding of the antibody to its antigen. Additionally, such methods can be used to make amino acid substitutions or deletions of one or more variable region cysteine residues participating in an intrachain disulfide bond to generate an antibody molecule lacking one or more intrachain disulfide bonds. Other alterations to a polynucleotide are encompassed by the present invention and will be known to those of ordinary skill of the art upon consideration of the present disclosure.

In addition, techniques developed for the production of "chimeric antibodies" (Morrison et al., (1984) *Proc. Natl. Acad. Sci. USA* 81:851–855; Neuberger et al., (1984) *Nature* 312:604–608; Takeda et al., (1985) *Nature* 314:452–454) by splicing genes from a mouse antibody molecule of appropriate antigen specificity together with genes from a human antibody molecule of appropriate biological activity can be generated and employed in the present invention. As described herein, a chimeric antibody is a molecule in which different portions are derived from different animal species, such as those having a variable region derived from a murine mAb and a human immunoglobulin constant region, e.g., humanized antibodies.

Alternatively, techniques for the production of single chain antibodies are known (see, e.g., U.S. Pat. No. 4,946,778; Bird, (1988) *Science* 242:423–42; Huston et al., (1988) *Proc. Natl. Acad. Sci. U.S.A.* 85:5879–5883; and Ward et al., (1989) *Nature* 334:544–54) and can be adapted to produce single chain antibodies. Single chain antibodies can be formed by linking the heavy and light chain fragments of the Fv region via an amino acid bridge, resulting in a single chain polypeptide. Techniques for the assembly of functional Fv fragments in *E. coli* can also be used (Skerra et al., (1988) *Science* 242:1038–1041).

A clone encoding an antibody of the present invention can be obtained according to the methods described herein and known to those of ordinary skill in the art.

V. Methods of Producing Antibodies of the Present Invention

The antibodies of the present invention can be produced by any method known in the art for the synthesis of antibodies, in particular, by chemical synthesis or by recombinant expression techniques. The following is presented in addition to the discussion herein above regarding antibody production.

V.A. Recombinant

Recombinant expression of an anti-P2Y10 antibody of the present invention, or a fragment, derivative or analog thereof, (e.g., a heavy or light chain of an antibody of the present invention or a single chain anti-P2Y10 antibody of the present invention), requires the construction of an expression vector comprising a polynucleotide that encodes such an antibody. Once a polynucleotide encoding an antibody molecule or a heavy or light chain of an antibody, or portion thereof (for example comprising a heavy or light chain variable domain) of the present invention has been obtained, a vector for the production of the antibody molecule can be produced by recombinant DNA technology using techniques known in the art. Methods for preparing a protein by expressing a polynucleotide containing an antibody-encoding nucleotide sequence are described herein.

Methods known to those of ordinary skill in the art can be used to construct expression vectors containing antibody coding sequences and appropriate transcriptional and translational control signals. These methods include, for example, in vitro recombinant DNA techniques, synthetic techniques, and in vivo genetic recombination. The present invention, thus, encompasses replicable vectors comprising a nucleotide sequence encoding an antibody molecule of the present invention, or a heavy or light chain thereof, or a heavy or light chain variable domain, operably linked to a promoter. Such vectors can include the nucleotide sequence encoding the constant region of an antibody molecule (see, e.g., PCT Publication WO 86/05807; PCT Publication WO 89/01036; and U.S. Pat. No. 5,122,464), and a variable domain of the antibody can be cloned into such a vector for expression of the entire heavy or light chain.

The expression vector is transferred to a host cell by conventional techniques and the transfected cells are then cultured by conventional techniques to produce an antibody of the present invention. Thus, the present invention comprises host cells containing a polynucleotide encoding an antibody of the present invention, or a heavy or light chain thereof, or a single chain antibody of the present invention, operably linked to a heterologous promoter. In representative embodiments for the expression of double-chained antibodies, vectors encoding both the heavy and light chains may be co-expressed in the host cell for expression of the entire immunoglobulin molecule, as detailed herein.

A variety of host-expression vector systems can be employed to express an antibody molecule of the present invention. Such host-expression systems represent vehicles by which a coding sequence of interest can be produced and subsequently purified, but also represent cells that may, when transformed or transfected with the appropriate nucleotide coding sequences, express an antibody molecule of the present invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, (CaMV); tobacco mosaic virus, (TMV)) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Under some conditions it might be desirable that bacterial cells such as *Escherichia coli*, or eukaryotic cells are used for the expression of a recombinant antibody molecule, especially for the expression of whole recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., (1986) *Gene* 45:101; Cockett et al., (1990) *Bio/Technology* 8:2).

In bacterial systems, a number of expression vectors can be advantageously employed, depending upon the use intended for the antibody molecule being expressed. For example, when a large quantity of such a protein is to be produced, for example for the generation of a pharmaceutical composition comprising an antibody molecule (such an anti-P2Y10 antibody, as described herein), vectors that direct the expression of high levels of fusion protein products that are readily purified can be desirable. Such vectors include, but are not limited, to the *E. coli* expression vector pUR278 (Ruther et al., (1983) *EMBO J.* 2:1791), in which the antibody coding sequence can be ligated individually into the vector in frame with the lac Z coding region so that a fusion protein is produced; pIN vectors (Inouye & Inouye, (1985) *Nucleic Acids Res.* 13:3101–3109; Van Heeke & Schuster, (1989) *J. Biol. Chem.* 24:5503–5509); and the like. pGEX vectors can also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or Factor Xa protease cleavage sites so that the cloned target gene product can be released from the GST moiety.

In an insect system, *Autographa californica* nuclear polyhedrosis virus (AcNPV) can be used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (see, e.g., Logan & Shenk, (1984) *Proc. Natl. Acad. Sci. U.S.A.* 81:355–359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., (1987) *Method Enzymol.* 153:51–544).

In addition, a host cell strain can be chosen that modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines that stably express the antibody molecule can be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the antibody molecule. Such engineered cell lines may be particularly useful in screening and evaluation of compounds that interact directly or indirectly with the antibody molecule.

A number of selection systems can be used. For example, the herpes simplex virus thymidine kinase (Wigler et al., (1977) *Cell* 11:223), hypoxanthine-guanine phosphoribosyltransferase (Szybalska & Szybalski, (1992) *Proc. Natl. Acad. Sci. U.S.A.* 48:202), and adenine phosphoribosyltransferase (Lowy et al., (1980) *Cell* 22:817) genes can be employed in tk-, hgprt- or aprt-cells, respectively. Also, antimetabolite resistance can be used as the basis of selection for the following genes: dhfr, which confers resistance to methotrexate (Wigler et al., (1980) *Proc. Natl. Acad. Sci. U.S.A.* 77:357; O'Hare et al., (1981) *Proc. Natl. Acad. Sci. U.S.A.* 78:1527); gpt, which confers resistance to mycophenolic acid (Mulligan & Berg, (1981) *Proc. Natl. Acad. Sci. U.S.A.* 78:2072); neo, which confers resistance to the aminoglycoside G-418 (*Clinical Pharmacy* 12:488–505; Wu & Wu, (1991) *Biotherapy* 3:87–95; Tolstoshev, (1993) *Ann. Rev. Pharmacol. Toxicol.* 32:573–596; Mulligan, (1993) *Science* 260:926–932; and Morgan & Anderson, (1993) *Ann. Rev. Biochem.* 62:191–217; *TIB TECH* 11(5):155–215, May, 1993); and hygro, which confers resistance to hygromycin (Santerre et al., (1984) *Gene* 30:147). Methods known in the art of recombinant DNA technology can be applied to select the desired recombinant clone, and such methods are described, for example, in *Current Protocols in Molecular Biology*, (Ausubel et al., eds.), Greene Publishing Associates and Wiley-Interscience, New York (2002); Kriegler, *Gene Transfer and Expression, A Laboratory Manual*, Stockton Press, New York, N.Y., USA (1990); *Current Protocols in Human Genetics*, (Dracopoli et al., eds.), John Wiley & Sons, New York, N.Y., USA (1994), Chapters 12 and 13; and Colbere-Garapin et al., (1981) *J. Mol. Biol.* 150:1.

The expression levels of an antibody molecule can be increased by vector amplification (for a review, see Bebbington & Hentschel, in *DNA Cloning, vol. 3*, Academic Press, New York, N.Y., USA (1987)). When a marker in the vector system expressing antibody is amplifiable, an increase in the level of inhibitor present in culture of host cell will increase the number of copies of the marker gene. Since the amplified region is associated with the antibody gene, production of the antibody will also increase (Crouse et al., (1983) *Mol. Cell. Biol.* 3:257).

The host cell can be co-transfected with two expression vectors of the present invention, the first vector encoding a heavy chain-derived polypeptide and the second vector encoding a light chain-derived polypeptide. The two vectors can contain identical selectable markers that enable equal expression of heavy and light chain polypeptides. Alternatively, a single vector can be used which encodes, and is capable of expressing, both heavy and light chain polypeptides. In such situations, the light chain should be placed before the heavy chain to avoid an excess of toxic free heavy chain (Proudfoot, (1986) *Nature* 322:52; Kohler, (1980) *Proc. Natl. Acad. Sci. U.S.A.* 77:2197). The coding sequences for the heavy and light chains can comprise cDNA or genomic DNA.

Once an antibody molecule of the present invention has been produced by an animal, chemically synthesized, or recombinantly expressed, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

V.B. Phage Display Methods

An anti-P2Y10 antibody of the present invention can also be generated using various phage display methods known in the art. In phage display methods, functional antibody domains are displayed on the surface of phage particles that carry the polynucleotide sequences encoding them. In a particular embodiment, such phage particles can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make an antibody of the present invention include those disclosed in Brinkman et al., (1995) *J. Immunol. Methods* 182:41–50; Ames et al., (1995) *J. Immunol. Methods* 184: 177–186; Kettleborough et al., (1994) *Eur. J. Immunol.* 24:952–958; Persic et al., (1997) *Gene* 187 9–18; Burton et al., (1994) *Adv. Immunology* 57:191–280; PCT Publications PCT/GB91/01134; WO 90/02809; WO 91/10737; WO 92/01047; WO 92/18619; WO 93/11236; WO 95/15982; WO 95/20401; and in U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described herein. For example, techniques to recombinantly produce Fab, Fab' and F(ab')$_2$ fragments can also be employed using methods known in the art such as those disclosed in PCT Publication WO 92/22324; Mullinax et al., (1992) *BioTechniques* 12(6):864–869; and Sawai et al., (1995) *AJRI* 34:26–34; and Better et al., (1988) *Science* 240:1041–1043. Examples of techniques that can be used to produce single-chain Fv's and antibodies include those described in U.S. Pat. Nos. 4,946,778 and 5,258,498; Huston et al., (1991) *Method Enzymol.* 203:46–88; Shu et al., (1993) *Proc. Natl. Acad. Sci. USA* 90:7995–7999; and Skerra et al., (1988) *Science* 240:1038–1040.

For some uses, including in vivo use of antibodies in humans and in vitro detection assays, it can be desirable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art (see, e.g., Morrison, (1985) *Science* 229: 1202; Oi et al., (1986) *BioTechniques* 4:214; Gillies et al., (1989) *J. Immunol. Methods* 125:191–202; EP 171496; EP 173494; PCT Publications WO 8601533; WO 8702671; Boulianne et al., (1984) *Nature* 312:643; Neuberger et al., (1985) *Nature* 314:268; U.S. Pat. Nos. 5,807,715; 4,816,567; and 4,816,397).

VI. Hybridomas of the Present Invention

A hybridoma can be employed in the production of a monoclonal antibody of the present invention. Indeed, in one aspect of the present invention hybridoma strain PTA-3975 was prepared as described in the Examples. Hybridoma strain PTA-3975 produces an anti-P2Y10 antibody of the present invention. Similar hybridomas can be prepared and used to produce an antibody of the present invention. Representative methods of preparing a hybridoma for the production of a monoclonal antibody of the present invention follow.

In one example of a hybridoma-based method of producing an antibody, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent typically, but not necessarily, includes polypeptides of the present invention or a fusion protein thereof. In one example, the immunizing agent comprises a P2Y10 polypeptide-expressing cell (or a cell expressing a fragment thereof, such as P2Y10 residues 171–191; SEQ ID NOs:3 and 4). Such cells can be cultured in any suitable tissue culture medium; for example Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin. Generally, either peripheral blood lymphocytes (PBLs) are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, New York, N.Y., USA (1986), pp. 59–103). Immortalized cell lines are often transformed mammalian cells, particularly myeloma cells of rodent, bovine and human origin. Often, rat or mouse myeloma cell lines are employed. The hybridoma cells can be cultured in a suitable culture medium that can optionally comprise one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In some embodiments, preferred immortalized cell lines are those that fuse efficiently, support stable high level expression of antibody by the selected antibody-producing cells, and are sensitive to a medium such as HAT medium. Other useful immortalized cell lines are murine myeloma lines, which can be obtained, for instance, from the Salk Institute Cell Distribution Center, San Diego, Calif., USA and the American Type Culture Collection, Manassas, Va., USA. Yet other useful immortalized cell lines are the parent myeloma cell lines as provided by the ATCC. As noted and implied throughout the specification, human myeloma and mouse-human heteromyeloma cell lines also have been described for the production of human monoclonal antibodies (see, e.g., Kozbor, (1984) *J. Immunol.* 133:3001; Brodeur et al., *Monoclonal Antibody Production Techniques and Applications*, Marcel Dekker, Inc., New York, N.Y., USA (1987) pp. 51–63).

The culture medium in which the hybridoma cells are cultured can then be assayed for the presence of monoclonal antibodies directed against a P2Y10 polypeptide or a fragment thereof (such as P2Y10 residues 171–191). The binding specificity of monoclonal antibodies produced by the hybridoma cells can be determined, for example by immunoprecipitation or by an in vitro binding assay, such as radioimmunoassay (RIA) or enzyme-linked immunoabsorbant assay (ELISA). Such techniques are known in the art. The binding affinity of the monoclonal antibody can, for example, be determined by a Scatchard analysis (see Munson & Pollart, (1980) *Anal. Biochem.* 107:220.

After the desired hybridoma cells are identified, the clones can be subcloned by limiting dilution procedures and grown by standard methods (see, e.g., Goding, *Monoclonal Antibodies: Principles and Practice*, Academic Press, New York, N.Y., USA (1986) and/or Wands et al., (1981) *Gastroenterology* 80:225–232). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones can be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography, all of which techniques will be known to those of ordinary skill in the art.

VII. Representative Applications

The modulators of the present invention, particularly a modulator comprising an anti-P2Y10 antibody, can be used in a variety of applications. A representative, but non-limiting, list of applications for modulators of the present invention includes (a) activating a resting T lymphocyte; (b) inducing surface expression of P2Y10 on a resting T lymphocyte; (c) stimulating P2Y10 mRNA expression in a resting T lymphocyte; and (d) inhibiting proliferation of an activated T lymphocyte modulation of T lymphocyte activity and modulating the expression of P2Y10 on the surface of a T lymphocyte. Other applications include the purification, detection and targeting of a P2Y10 polypeptide, including both in vitro and in vivo diagnostic and therapeutic methods.

Further, the antibody modulators of the present invention can be used in immunoassays for qualitatively and quantitatively measuring expression levels and amounts of P2Y10 in a biological sample, such a population of PBMC's (see, e.g., Harlow et al., *Antibodies: A Laboratory Manual*, $2^{nd}$ ed., Cold Spring Harbor Laboratory Press, Cold Spring Harbor, N.Y., USA (1988)).

As discussed in more detail below, a modulator of the present invention, e.g., an anti-P2Y10 antibody, can be used either alone or in combination with other compositions. An antibody of the present invention can further be recombinantly fused to a heterologous polypeptide at the N- or C-terminus or chemically conjugated (including covalently and non-covalently conjugations) to a polypeptide or other composition. For example, an antibody of the present invention can be recombinantly fused or conjugated to molecules useful as labels in detection assays and effector molecules such as heterologous polypeptides, drugs, radionucleotides, or toxins (see, e.g., PCT Publications WO 92/08495; WO 91/14438; WO 89/12624; U.S. Pat. No. 5,314,995; and EP 396,387).

Further discussion of some representative applications of antibody modulators of the present invention follows. It is noted that although the following discussion is primarily directed to antibody modulators, the discussion is applicable mutatis mutandis to any modulator. It is implicit in the following discussion that the various methods and applications can be carried out in vivo or in vitro.

VII.A. Diagnostic Assays

An antibody, or a fragment thereof, of the present invention can be used in a diagnostic assay to detect the presence or absence of, or to quantify, an amount of a P2Y10 polypeptide or fragment thereof in a sample. Such a diagnostic assay can comprise at least two steps. The first step can comprise contacting a sample with an antibody of the present invention, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (see, e.g., Arenkov et al., (2000) *Anal. Biochem.* 278(2):123–131), or a chromatography column, etc. A second step can comprise quantifying an amount of antibody bound to the substrate. Alternatively, the method can optionally involve a step of attaching the antibody, for example covalently, electrostatically, or reversibly, to a solid support, and a second step of contacting the bound antibody with the sample, as defined above and elsewhere herein.

Antibodies can also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

VII.B. Protein Purification

An antibody, or fragments thereof, of the present invention can be fused to marker sequences, such as a peptide to facilitate purification of a protein, such as a P2Y10 polypeptide or a fragment thereof. In some embodiments, the marker amino acid sequence is a hexa-histidine peptide, such as the tag provided in a pQE vector (QIAGEN, Inc., Chatsworth, Calif., USA), among others, many of which are commercially available. As described in Gentz et al., (1989) *Proc. Natl. Acad. Sci. U.S.A.* 86:821–824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., (1984) *Cell* 37:767) and the FLAG® tag (Sigma, St. Louis, Mo., USA).

VII.C. Pharmaceutical Compositions

An antibody of the present invention, with or without a therapeutic agent conjugated to it, administered alone or in combination with a cytotoxic factor, a cytokine or other biologically active moiety, including a small molecule, can be used as a therapeutic.

An anti-P2Y10 antibody, or a fragment thereof, can be conjugated to a therapeutic moiety such as a cytotoxin, e.g., a cytostatic or cytocidal agent, a therapeutic agent or a radioactive metal ion, e.g., an alpha-emitter, such as, $^{213}$Bi. The terms "cytotoxin" and "cytotoxic agent" include any agent that is detrimental to cells. Examples of cytotoxins and cytotoxic agents include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Representative therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques for conjugating such therapeutic moiety to antibodies are known, (see, e.g., Arnon et al., in *Monoclonal Antibodies And Cancer Therapy*, (Reisfeld et al., eds.), Alan R. Liss, Inc., New York, N.Y., USA (1985) pp. 243–56; Hellstrom et al., in *Controlled Drug Delivery*, ($2^{nd}$ ed.), (Robinson et al., eds.), Marcel Dekker, Inc., new York, N.Y., USA (1987) pp. 623–53; Thorpe, in *Monoclonal Antibodies '84: Biological And Clinical Applications*, (Pinchera et al., eds.), (1985) pp. 475–506; *Monoclonal Antibodies For Cancer Detection And Therapy*, (Baldwin et al., eds), Academic Press, New York, N.Y., USA (1985) pp. 303–16, and Thorpe et al., (1982) *Immunol. Rev.* 62:119–58).

As well as the use of an antibody of the present invention as a therapeutic agent, the present invention also encompasses anti-P2Y10 antibodies, and fragments thereof, conjugated to a diagnostic agent. The antibodies can be used diagnostically, for example, to monitor the development or progression of a tumor as part of a clinical testing procedure, for example to determine the efficacy of a given treatment regimen. Detection can optionally be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody (or fragment thereof) or indirectly, through an intermediate (such as, for example, a linker known in the art) using techniques known in the art. See, for example, U.S. Pat. No. 4,741,900, disclosing metal ions that can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$ or $^{99}Tc$.

The present invention also provides pharmaceutical compositions that do not comprise antibodies. Such compositions comprise a therapeutically effective amount of a modulator of the present invention, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water and water-based formulations are desirable carriers when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences*, (Gennaro, ed.) 20th ed., Mack Publishing, Easton, Pa., USA (2000). Such compositions will contain a therapeutically effective amount of the modulator, for example in purified form, together with a suitable amount of carrier so as to provide the form for proper administration to the subject. The formulation should suit the mode of administration.

In one embodiment, a composition is formulated in accordance with routine procedures as a pharmaceutical composition adapted for intravenous administration to human beings. Typically, compositions for intravenous administration are solutions in sterile isotonic aqueous buffer. Where necessary, a composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a composition is to be administered by infusion, it can be dispensed with an infusion bottle containing sterile pharmaceutical grade water or saline. Where a composition is administered by injection, an ampoule of sterile water for injection or saline can be provided so that the ingredients may be mixed prior to administration.

The compounds of the present invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the present invention which will be effective in the treatment, inhibition and prevention of a disease or disorder associated with aberrant expression and/or activity of a polypeptide of the present invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems.

For antibodies, the dosage administered to a subject is typically 0.1 mg/kg to 100 mg/kg of the subject's body weight. Preferably, the dosage administered to a subject is between 0.1 mg/kg and 20 mg/kg of the subject's body weight, more preferably 1 mg/kg to 10 mg/kg of the subject's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the present invention might be reduced by enhancing uptake and tissue penetration (e.g., into the brain) of the antibodies by modifications such as, for example, lipidation.

A pharmaceutical composition can be administered in conjunction with a pharmaceutically acceptable carrier, diluent, or excipient, to achieve any of the above-described therapeutic uses and effects. Such pharmaceutical compositions can comprise agonists, antagonists, activators or inhibitors. The compositions can be administered alone, or in combination with at least one other agent or reagent, such as a stabilizing compound, which may be administered in any sterile, biocompatible pharmaceutical carrier, including, but not limited to, saline, buffered saline, dextrose, and water. The compositions may be administered to a patient alone, or in combination with other agents, drugs, hormones, or biological response modifiers.

The pharmaceutical compositions for use in the present invention can be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, vaginal, or rectal means.

In addition to the active ingredients, the pharmaceutical compositions can contain pharmaceutically acceptable/ physiologically suitable carriers or excipients comprising auxiliaries which facilitate processing of the active compounds into preparations that can be used pharmaceutically. Further details on techniques for formulation and administration are provided in *Remington's Pharmaceutical Sciences*, (Gennaro, ed.) 20th ed., Mack Publishing, Easton, Pa., USA (2000).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

In addition, pharmaceutical preparations for oral use can be obtained by the combination of active compounds with a solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropyl-methylcellulose, or sodium carboxymethylcellulose; gums, including arabic and tragacanth, and proteins such as gelatin and collagen. If desired, disintegrating or solubilizing agents may be added, such as cross-linked polyvinyl pyrrolidone, agar, alginic acid, or a physiologically acceptable salt thereof, such as sodium alginate.

Dragee cores may be used in conjunction with physiologically suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification, or to characterize the quantity of active compound, i.e., dosage.

Pharmaceutical preparations, which can be used orally, further include push-fit capsules made of gelatin, as well as soft, scaled capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances, which increase the viscosity of the suspension, such as sodium carboxymethyl cellulose, sorbitol, or dextran. In addition, suspensions of the active compounds may be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension may also contain suitable stabilizers or agents that increase the solubility of the compounds to allow for the preparation of highly concentrated solutions.

For topical or nasal administration, penetrants or permeation agents (enhancers) that are appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

A pharmaceutical composition may be provided as a salt and can be formed with many acids, including but not limited to, hydrochloric, sulfuric, acetic, lactic, tartaric, malic, succinic, and the like. Salts tend to be more soluble in aqueous solvents, or other protonic solvents, than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, combined with a buffer prior to use. After the pharmaceutical compositions have been prepared, they can be placed in an appropriate container and labeled for treatment of an indicated condition. For administration of a modulator, such labeling can include guidance on the amount, frequency, and method of administration.

Pharmaceutical compositions suitable for use in the present invention include compositions wherein the active ingredients are contained in an effective amount to achieve the intended purpose. The determination of an effective dose or amount is well within the capability of those skilled in the art. For any compound, the therapeutically effective dose can be estimated initially either in cell culture assays, for example, using neoplastic cells, or in animal models, usually mice, rabbits, dogs, or pigs. The animal model may also be used to determine the appropriate concentration range and route of administration. Such information can then be used and extrapolated to determine useful doses and routes for administration in humans.

A therapeutically effective dose refers to that amount of active ingredient (e.g., a modulator of the present invention) that ameliorates, reduces, diminishes, or eliminates the symptoms or condition. Therapeutic efficacy and toxicity can be determined by standard pharmaceutical procedures in cell cultures or in experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, which can be expressed as the ratio, $LD_{50}/ED_{50}$. Pharmaceutical compositions that exhibit large therapeutic indices are preferred. The data obtained from cell culture assays and animal studies are used in determining a range of dosages for human use. A representative dosage contained in a pharmaceutical composition is within a range of circulating concentrations that include the $ED_{50}$ with little or no toxicity. The dosage varies within this range depending upon the dosage form employed, the sensitivity of the patient, and the route of administration.

The practitioner, who will consider the factors related to an individual requiring treatment, will determine the exact dosage. Dosage and administration are adjusted to provide sufficient levels of the active component, or to maintain the desired effect. Factors which may be taken into account include the severity of the individual's disease state; the general health of the patient; the age, weight, and gender of the patient; diet; time and frequency of administration; drug combination(s); reaction sensitivities; and tolerance/response to therapy. As a general guide, long-acting pharmaceutical compositions may be administered every 3 to 4 days, every week, or once every two weeks, depending on half-life and clearance rate of the particular formulation. Variations in these dosage levels can be adjusted using standard empirical routines for optimization, as is well understood in the art.

As a guide, normal dosage amounts may vary from 0.1 to 100,000 micrograms (μg), up to a total dose of about 1 gram (g), depending upon the route of administration. Guidance as to particular dosages and methods of delivery is provided in the literature and is generally available to practitioners in the art. Those skilled in the art will employ different formulations for nucleotides than for proteins or their inhibitors or activators. Similarly, the delivery of polynucleotides or polypeptides will be specific to particular cells, conditions, locations, and the like.

The present invention also provides a pharmaceutical pack or kit comprising one or more containers filled with one or more of the ingredients of the pharmaceutical compositions of the present invention. Optionally a notice can be associated with such container(s) in the form prescribed by a governmental agency regulating the manufacture, use or sale of pharmaceuticals or biological products, which notice reflects approval by the agency of manufacture, use or sale for human administration. Such a notice can also provide guidance on how to use the pack or kit.

VII.D. P2Y10 Modulators

The present invention broadly encompasses modulators of P2Y10. Such modulators can act as agonists or antagonists. A P2Y10 modulator can be employed in the various methods of the present invention. Such modulators can comprise for example, one, or a combination of, a polypeptide of variable length (including antibodies and fusion proteins) and a small molecule.

In one aspect of the present invention, a P2Y10 modulator that associates specifically with a P2Y10 polypeptide, e.g., an anti-P2Y10 antibody, is described. Such a modulator has one or more properties selected from the group consisting of: (a) the ability to activate a resting T lymphocyte upon association with a P2Y10 polypeptide; (b) the ability to cause expression of a P2Y10 polypeptide on the surface of a resting T lymphocyte upon association with a P2Y10 polypeptide; (c) the ability to stimulate expression of mRNA encoding a P2Y10 polypeptide in a resting T lymphocyte upon association with a P2Y10 polypeptide; and (d) the ability to inhibit proliferation of an activated T lymphocyte upon association with a P2Y10 polypeptide.

A modulator can comprise any type of chemical entity, such as a protein of any size, a small molecule or an antibody. An example of a modulator that is an antibody is presented herein, notably in the Examples. Just as there is no limitation on whether a modulator augments or inhibits P2Y10 or P2Y10-mediated activity, there is no limitation on the mechanism by which a modulator of P2Y10 acheives such an effect. For example, as further described herein, a modulator might block a ligand (e.g., an interleukin or other molecule secreted from, or present in, a mixture of PBMC's) from associating with a P2Y10 polypeptide. In another case, a modulator might inhibit a P2Y10 polypeptide from associating with another polypeptide expressed on the surface of a T lymphocyte. In yet another case, a modulator might facilitate the association of a P2Y10 polypeptide with another polypeptide expressed on the surface of a T lymphocyte.

A modulator of the present invention can comprise a fusion protein. As one of ordinary skill in the art will appreciate, and as discussed herein, a modulator of the present invention can be fused to a polypeptide sequence. For example, a modulator of the present invention can be fused with the constant domain of immunoglobulins (IgA, IgE, IgG, IgM), or portions thereof (CH1, CH2, CH3, or any combination thereof and portions thereof) resulting in chimeric polypeptides. Such fusion proteins can facilitate purification and can increase half-life in vivo. This has been shown for chimeric proteins consisting of the first two domains of the human CD4-polypeptide and various domains of the constant regions of the heavy or light chains of mammalian immunoglobulins (see, e.g., EP 394,827; Traunecker et al., (1988) *Nature* 331:84–86). Enhanced delivery of an antigen across the epithelial barrier to the immune system has been demonstrated for antigens (e.g., insulin) conjugated to an FcRn binding partner such as IgG or Fc fragments (see, e.g., PCT Publication WO 96/22024 and PCT Publication WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone (see, e.g., Fountoulakis et al., (1995) *J. Biochem.* 270:3958–3964). In one example, nucleic acids encoding a modulator can also be recombined with a gene of interest as an epitope tag (e.g., the hemagglutinin (HA) tag or FLAG® tag) to aid in detection and purification of the expressed polypeptide. For example, a system described by Janknecht et al. allows for the ready purification of non-denatured fusion proteins expressed in human cell lines (Janknecht et al., (1991) *Proc. Natl. Acad. Sci. USA* 88:8972–8976). In this system, the gene of interest is subcloned into a vaccinia recombination plasmid such that the open reading frame of the gene is translationally fused to an amino-terminal tag consisting of six histidine residues. The tag serves as a matrix binding domain for the fusion. Extracts from cells infected with the recombinant vaccinia virus are loaded onto $Ni^{2+}$ nitriloacetic acid-agarose column and histidine-tagged proteins can be selectively eluted with imidazole-containing buffers.

Regardless of whether a given P2Y10 modulator is a small molecule, antibody or polypeptide, a modulator of the present invention can have one or more properties selected from the group consisting of (a) the ability to activate a resting T lymphocyte upon association with a P2Y10 polypeptide; (b) the ability to induce expression of a P2Y10 polypeptide on the surface of a resting T lymphocyte upon association with a P2Y10 polypeptide; (c) the ability to stimulate expression of mRNA encoding a P2Y10 polypeptide in a resting T lymphocyte upon association with a P2Y10 polypeptide; and (d) the ability to inhibit proliferation of an activated T lymphocyte upon association with a P2Y10 polypeptide.

When a P2Y10 modulator is an antibody, the antibody can associate specifically with P2Y10, for example residues 171–191 of a P2Y10 polypeptide (SEQ ID NOs:3 and 4). Such an antibody can be produced by a known or generated hybridoma strain such as PTA-3975, for example.

VII.D.1. Antibodies of the Present Invention as Modulators

An antibody of the present invention can bind an antigen comprising an antigenic epitope (e.g., a P2Y10 polypeptide), or a portion thereof (e.g., residues 171–191 of a P2Y10 polypeptide; SEQ ID NOs:3 and 4). A P2Y10 antibody of the present invention may act as an agonist or an antagonist (i.e., a modulator) of a P2Y10 polypeptide particularly, and more generally as an agonist or antagonist of a biological activity induced, mediated or inhibited by a P2Y10 polypeptide. The effect of the antibody, whether agonizing or antagonizing, can be a function of the state (resting or activated) of a T lymphocyte on which the P2Y10 is expressed or not expressed, as described herein.

Continuing, in one embodiment an antibody of the present invention can act as an agonist or an antagonist (i.e., a modulator) of an effect mediated by a P2Y10 polypeptide, such as T lymphocyte activation or the inhibition of the proliferation of T lymphocytes. For example, the present invention includes antibodies that may disrupt an interaction between a ligand or receptor and a P2Y10 polypeptide, either partially or fully. Such a disruption can be an agonizing or antagonizing interaction and, in some embodiments, can depend on the state of a T lymphocyte on the surface of which the P2Y10 polypeptide is expressed (e.g., activated or resting).

P2Y10 activation (e.g., signaling events initiated or perpetuated by P2Y10) can be determined by techniques described herein or otherwise known in the art. For example, P2Y10 activation can be determined by detecting the phosphorylation state of P2Y10 or its substrate (e.g., whether a given site, such as a tyrosine or serine/threonine residue is phosphorylated) by immunoprecipitation followed by western blot analysis.

In another embodiment of the present invention, antibodies are provided that may inhibit ligands binding to P2Y10 and thereby modulate P2Y10-mediated activity by at least 95%, at least 90%, at least 85%, at least 80%, at least 75%, at least 70%, at least 60%, or at least 50% of the activity in absence of the antibody, thereby antagonizing or agonizing a biological activity.

When a P2Y10 modulator is an antibody, the antibody can specifically associate with a P2Y10 polypeptide, but need not associate with any particular portion of a P2Y10 polypeptide. In one example, an antibody can associate with residues 171–191 of a P2Y10 polypeptide (SEQ ID NOs:3 and 4).

An antibody modulator can be produced in any of a variety of ways, as described herein. In one embodiment, an anti-P2Y10 antibody modulator is produced by a hybridoma, such as hybridoma strain PTA-3975, which is a rat hybridoma.

An antibody modulator of the present invention can have one or more of the following properties: (a) the ability to activate a resting T lymphocyte; (b) the ability to induce surface expression of P2Y10 on a resting T lymphocyte; (c) the ability to stimulate P2Y10 mRNA expression in a resting T lymphocyte; and (d) the ability to inhibit proliferation of an activated T lymphocyte. Each of these properties is discussed more fully herein below.

A modulator can have the ability to activate a resting T lymphocyte upon association with a P2Y10 polypeptide. T lymphocyte activation assays, such as those that measure T lymphocyte proliferation, are known in the art (see, e.g., Ledbetter et al., (1990) *Blood* 75:1531–39; Siefken et al., (1997) *Cell. Immunol.* 176:59–65). When a modulator is an anti-P2Y10 antibody, association of an anti-P2Y10 antibody with a P2Y10 polypeptide is a natural result of exposing one to another, although such a binding event can be verified, if desired, using binding assays known in the art. The resting T lymphocyte can be isolated or can be a member of a population of PBMC's. Methods of preparing PBMC's from blood are known (e.g., by density gradient cetrifugation).

Another property a modulator can have is the ability to induce expression of a P2Y10 polypeptide on the surface of a resting T lymphocyte upon association with a P2Y10 polypeptide. Expression of a P2Y10 polypeptide on the surface of a T lymphocyte can be detected as described herein, for example by FACS-based techniques. An assessment of P2Y10 expression can be made, for example, by performing a FACS analysis of a resting T lymphocyte population to determine an amount of expressed P2Y10, followed by a FACS analysis of the population of T lymphocytes after exposure to an anti-P2Y10 antibody.

Yet another property a modulator can have is the ability to stimulate expression of mRNA encoding a P2Y10 polypeptide in a resting T lymphocyte upon association with a P2Y10 polypeptide. Expression of mRNA encoding a P2Y10 polypeptide can be quantitated in any way, for example, by employing a binding assay or by employing a labeled anti-P2Y10 antibody of the present invention.

A further property a modulator can have is the ability to inhibit proliferation of an activated T lymphocyte upon association with a P2Y10 polypeptide. A T lymphocyte can be activated in any way, for example by exposing the T lymphocyte to phorbol ester, anti-CD3 antibodies, anti-CD28 antibodies or a combination of anti-CD3 and anti-CD28 antibodies, as described herein. T lymphocyte proliferation can be conveniently measured by employing a tritium-labled thymidine incorporation assay, such as that described herein.

A modulator of the present invention can have one or a combination of two or more of the properties discussed above.

As noted herein, modulation can be performed in vivo or in vitro. Representative systems for both in vivo and in vitro modulation protocols are provided herein.

VII.E. Modulation of a Biological Activity

A modulator of the present invention, such as an anti-P2Y10 antibody of the present invention, can be employed to modulate a biological activity. The term "biological activity" includes any activity induced, mediated or inhibited by P2Y10 binding, for example, T lymphocyte activation and/or proliferation, and upregulation and/or downregulation of an immune response. Modulation of a biological activity can be achieved by employing an anti-P2Y10 antibody alone, in combination with one or more additional therapeutics or drug moieties, or as a conjugate comprising a therapeutic or drug moeity. A conjugate of the present invention can be used to modify a given biological response, and the therapeutic agent or drug moiety is not to be construed as limited to classical chemical therapeutic agents. For example, a drug moiety can be a protein or polypeptide possessing a desired biological activity. Such proteins can include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (see, PCT Publication WO 97/33899), AIM II (see, PCT Publication WO 97/34911), Fas Ligand (Takahashi et al., (1994) *Int. Immunol.* 6:1567–1574), VEGI (see, PCT Publication WO 99/23105), a thrombotic agent or an anti-angiogenic agent, e.g., angiostatin or endostatin; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

Modulation of a biological activity can encompass, for example, (a) activation of a resting T lymphocyte upon association with a P2Y10 polypeptide; (b) inducing the expression of a P2Y10 polypeptide on the surface of a resting T lymphocyte upon association with a P2Y10 polypeptide; (c) stimulating expression of mRNA encoding a P2Y10 polypeptide in a resting T lymphocyte upon association with a P2Y10 polypeptide; or (d) inhibiting proliferation of an activated T lymphocyte upon association with a P2Y10 polypeptide.

Additionally, the modulation of a biological activity can be practiced in vivo or in vitro. When modulation is performed in vitro, the modulation can be performed as described in the Examples provided herein below. When modulation is performed in vivo, the modulation can be performed and detected in a subject, such as a mouse, rat or rabbit.

Examples of the modulation of some representative biological activities follow.

VII.E.1. Method of Activating a Resting T Lymphocyte

In another aspect of the present invention, a modulator of the present invention can be employed to activate a resting T lymphocyte and can be practiced in vitro or in vivo. As discussed herein, such a method may be employed in the treatment of a condition such as cancer, a viral infection, such as HIV, a bacterial infection, or any other condition in which it might be advantageous to augment an immune response.

In one embodiment of the method, a resting T lymphocyte is contacted with a modulator of a P2Y10 polypeptide. A P2Y10 modulator can be a modulator as described herein, including, for example, an antibody. As demonstrated in the Examples and Tables, exposure of a resting T lymphocyte to a modulator comprising an anti-P2Y10 antibody leads to T cell proliferation. When a modulator is an antibody, it can be isolated, for example, from a hybridoma such as strain PTA-3975 and can associate with a particular epitope on a P2Y10 polypeptide, such as residues 171–191 (SEQ ID NOs:3 and 4). Alternatively, such an antibody can be isolated from a hybridoma prepared as described herein. Other modulators can be isolated from biological sources or prepared synthetically.

VII.E.2. Method of Inducing Expression of a P2Y10 Polypeptide on the Surface of a T Lymphocyte In a further aspect of the present invention, a method of inducing expression of a P2Y10 polypeptide on the surface of a T lymphocyte is disclosed. The method can be performed in vivo or in vitro. In one embodiment of the method, a resting T lymphocyte is contacted with a P2Y10 modulator. The method may be useful, for example, in the treatment of immune conditions in which P2Y10 expression is inhibited naturally or by a non-native inhibitor. The method may also be useful in the treatment of disorders that are characterized by an unacceptably low level of a T lymphocyte-dependent immune response. Such conditions can include cancer, viral infections such as HIV and bacterial infections, to name just a few.

Representative P2Y10 modulators are described herein and can be employed in the method. One example of a P2Y10 modulator is an anti-P2Y10 antibody secreted by hybridoma strain PTW-3975. In this example, the antibody can bind specifically to residues 171–191 of P2Y10. Other examples of modulators include small molecules, proteins and nucleic acids.

The contacting can be carried out by any of a variety of approaches, the details of which can be dependent on the local environment of the T lymphocyte. For example, T lymphocytes, which can be isolated or a component in a heterogeneous population of cells, can be washed with PBS and then incubated with a modulator under suitable conditions.

If and/or when it is desired to detect the expression of a P2Y10 polypeptide on the surface of a T lymphocyte, a FACS-based approach can be employed and can optionally form a component of the contacting. By way of example, T lymphocytes can be washed with PBS containing FBS (FACS buffer) and then contacted with a modulator, such as an anti-P2Y10 antibody of the present invention, under suitable conditions (e.g., 30 minutes on ice). The cells can then be washed, labled with FITC or other agent, contacted with anti-CD4 or anti-CD8 antibodies and analyzed by FACS.

VII.E.3. Method of Upregulating Transciption of P2Y10 mRNA in a T Lymphocyte In a related aspect, the present invention also encompasses a method of upregulating transcription of P2Y10 mRNA in a T lymphocyte. The method comprises, in one embodiment, contacting a T lymphocyte with a modulator of P2Y10. The method may be useful, for example, in the treatment of immune conditions in which P2Y10 expression is inhibited naturally or by a non-native inhibitor.

Representative P2Y10 modulators are described herein and can be employed in the method. One example of a P2Y10 modulator is an anti-P2Y10 antibody secreted by hybridoma strain PTW-3975. In this example, the antibody can bind specifically to residues 171–191 of P2Y10. Other examples of modulators include small molecules, proteins and nucleic acids.

The contacting can be carried out by any of a variety of approaches, the details of which can be dependent on the local environment of the T lymphocyte. For example, T lymphocytes, which can be isolated or a component in a heterogeneous population of cells, can be washed with PBS and then incubated with a modulator under suitable conditions.

When it is desired to detect a degree to which transcription of P2Y10 mRNA is upregulated, any known method can be employed (see, e.g., Sambrook et al., *Molecular Cloning: A Laboratory Manual*, (3$^{rd}$ ed.) Cold Spring Harbor Laboratory Press, Cold Spring Harbor, N.Y., USA (2001), and *Current Protocols in Molecular Biology*, (Ausubel et al., eds.), Greene Publishing Associates and Wiley-Interscience, New York, N.Y., USA (2002)), including various commercially available instruments and kits prepared for this purpose (e.g., TAQMAN, available from Applied Biosystems, Foster City, USA).

VII.E.4. Method of Inhibiting Proliferation of an Activated T Lymphocyte

In still another aspect, the present invention comprises a method of inhibiting the proliferation of an activated T lymphocyte. In one embodiment the method comprises contacting an activated T lymphocyte with a modulator of a P2Y10 polypeptide. The method may also be useful in the treatment of disorders that are characterized by an unacceptably high level of a T lymphocyte-dependent immune response. Such conditions include, for example, rheumatoid arthritis, psoriatic arthritis, multiple sclerosis, juvenile diabetes, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia areata, autoimmune alopecia, autoimmune hypopituatarism, Guillain-Barre syndrome, and alveolitis, T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, asthma, acute respiratory distress syndrome, Sezary's syndrome and vascular diseases which have an inflammatory and or a proliferatory component such as restenosis, stenosis and artherosclerosis.

Inflammatory or immune associated diseases or disorders also includes, but is not limited to: endocrine disorders, rheumatic disorders, collagen diseases, dermatologic disease, allergic disease, opthalmic disease, respiratory disease, hematologic disease, gastrointestinal disease, inflammatory disease, autoimmune disease, congenital adrenal hyperplasia, nonsuppurative thyroiditis, hypercalcemia associated with cancer, psoriatic arthritis, rheumatoid arthritis, including juvenile rheumatoid arthritis, ankylosing spondylitis, acute and subacute bursitis, acute nonspecific tenosynovitis, acute gouty arthritis, post-traumatic osteoarthritis, synovitis of osteoarthritis, epicondylitis, systemic lupus erythematosus, acute rheumatic carditis, pemphigus, bullous dermatitis herpetiformis, severe erythema multiforme, exfoliative dermatitis, psoriasis, seborrheic dermatitis, seasonal or perennial allergic rhinitis, serum sickness, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, ulcerative colitis, regional enteritis, autoimmune vasculitis, multiple sclerosis, myasthenia gravis, anklyosing spondylitis, chronic obstructive pulmonary disease, solid organ transplant rejection, sepsis, and allergy.

A T lymphocyte can be activated in any of the range of activation methods known to those of skill in the art and/or described herein. For example, a T lymphocyte can be activated by incubating T lymphocytes, which can be isolated or a component of heterogenous mixture such as a population of PBMC's, with, for example, phorbol myristate acetate (PMA) or anti-CD3 (Ledbetter et al., (1986) *J. Immunol.* 136:3945–3952).

Representative P2Y10 modulators are described herein and can be employed in the method. One example of a P2Y10 modulator is an anti-P2Y10 antibody secreted by hybridoma strain PTW-3975. In this example, the antibody can bind specifically to residues 171–191 of P2Y10. Other examples of modulators include small molecules, proteins and nucleic acids.

The contacting can be carried out by any of a variety of approaches, the details of which can be dependent on the local environment of the T lymphocyte. For example, T lymphocytes, which can be isolated or a component in a heterogeneous population of cells, can be washed with PBS and then incubated with a modulator under suitable conditions.

A degree of T lymphocyte proliferation can be determined, for example, by monitoring uptake and/or incorporation of a detectable lable into lymphocytes undergoing clonal expansion. In one particular embodiment, a degree of proliferation can be identified by determing an amount of [$^3$H]-thymidine incorporated into clonally expanding cells by liquid scintillation counting.

VII.F. Method of Modulating an Immune Response

The present invention also encompasses a method of modulating an immune response. In one embodiment, the method comprises contacting a T lymphocyte with a modulator of P2Y10. This method can be employed, for example, to upregulate an immune response. Alternatively, a modulator of P2Y10 can be contacted with an activated T lymphocyte in order to inhibit proliferation of T lymphocytes and thus downregulate an immune response. The method can be carried out in vitro or in vivo. When the method is performed in vivo, the modulator can be disposed in a pharmaceutical composition as described herein and the contacting can be achieved by administering the pharmaceutical composition as described herein.

As used herein, the term "immune response" encompasses any detectable response initiating with, or perpetuated by, a cell or molecule normally having a physiological role in a mammalian immune system. Examples of immune response include T lmyphocyte activation, clonal expansion of T lymphocytes, as well as secretion and/or binding of interleukins and other messengers.

Representative P2Y10 modulators are described herein and can be employed in the method. One example of a P2Y10 modulator is an anti-P2Y10 antibody secreted by hybridoma strain PTW-3975. In this example, the antibody can bind specifically to residues 171–191 of P2Y10. Other examples of modulators include small molecules, proteins and nucleic acids.

The contacting can be carried out by any of a variety of approaches, the details of which can be dependent on the local environment of the T lymphocyte. For example, T lymphocytes, which can be isolated or a component in a heterogeneous population of cells, can be washed with PBS and then incubated with a modulator under suitable conditions.

VII.G. Method of Treating an Immune Disease

The present invention can also be employed in the treatment of an immune disease, as described herein above. For example, the present invention can be employed in situations in which a subject's immune system is depressed and it is desired to enhance the activity and/or efficiency of a subject's immune system. Such a situation might occur, for example, in the case of a subject afflicted with a viral infection, such as HIV, cancer, a bacterial infection or other immune system-impairing condition. Alternatively, the present invention can also be employed in sitations in which a subject's immune system is upregulated and is operating at a hypersensitive level. In such situations, it might be desirable to downregulate the subject's immune response. Examples of such conditions include, for example, rheumatoid arthritis, psoriatic arthritis, multiple sclerosis, juvenile diabetes, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia areata, autoimmune alopecia, autoimmune hypopituatarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, asthma, acute respiratory distress syndrome, Sezary's syndrome and vascular diseases which have an inflammatory and or a proliferatory component such as restenosis, stenosis and artherosclerosis.

Inflammatory or immune associated diseases or disorders also includes, but is not limited to: endocrine disorders, rheumatic disorders, collagen diseases, dermatologic disease, allergic disease, opthalmic disease, respiratory disease, hematologic disease, gastrointestinal disease, inflammatory disease, autoimmune disease, congenital adrenal hyperplasia, nonsuppurative thyroiditis, hypercalcemia associated with cancer, psoriatic arthritis, rheumatoid arthritis, including juvenile rheumatoid arthritis, ankylosing spondylitis, acute and subacute bursitis, acute nonspecific tenosynovitis, acute gouty arthritis, post-traumatic osteoarthritis, synovitis of osteoarthritis, epicondylitis, systemic lupus erythematosus, acute rheumatic carditis, pemphigus, bullous dermatitis herpetiformis, severe erythema multiforme, exfoliative dermatitis, psoriasis, seborrheic dermatitis, seasonal or perennial allergic rhinitis, serum sickness, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, ulcerative colitis, regional enteritis, autoimmune vasculitis, multiple sclerosis, myasthenia gravis, anklyosing spondylitis, chronic obstructive pulmonary disease, solid organ transplant rejection, sepsis, and allergy.

Immune diseases associated with or secondary to other diseases can also be treated. Such diseases and conditions include recombinase activating gene (RAG 1/2) deficiency, adenosine deaminase (ADA) deficiency, interleukin receptor chain (c) deficiency, Janus-associated kinase 3 (JAK3) deficiency, reticular dysgenesis, DiGeorge syndrome, nude syndrome, T cell receptor deficiency, MHC class II deficiency, TAP-2 deficiency (MHC class I deficiency), ZAP70 tyrosine kinase deficiency, purine nucleotide phosphorylase (PNP) deficiency, X-linked agammaglobulinemia (Bruton's tyrosine kinase deficiency), autosomal recessive agammaglobulinemia: Mu heavy chain deficiency, surrogate light chain (5/14.1) deficiency), Hyper-IgM syndrome: X-linked (CD40 ligand deficiency), Ig heavy chain gene deletions, IgA deficiency, selective deficiency of IgG subclasses (with or without IgA deficiency), common variable immunodeficiency (CVID), antibody deficiency with normal immunoglobulins, transient hypogammaglobulinemia of infancy, interferon receptor (IFNGR1, IFNGR2) deficiency, Interleukin 12 and interleukin 12 receptor deficiency, immunodeficiency with thymoma, Wiskott-Aldrich syndrome (WAS protein deficiency), ataxia telangiectasia (ATM deficiency), X-linked lymphoproliferative syndrome (SH2D1A/SAP deficiency), hyper IgE syndrome, Bloom syndrome, xeroderma pigmentosum, Fanconi anemia, ICF syndrome, Nijmegen breakage syndrome, Seckel syndrome, Down syndrome (Trisomy 21), Turner syndrome, deletions or rings of chromosome 18 (18p- and 18q-), short-limbed skeletal dysplasia (short-limbed dwarfism), cartilage-hair hypoplasia (metaphyseal chondroplasia), Schimke immuno-osseous dysplasia, Dubowitz syndrome, kyphomelic dysplasia with SCID, Mulibrey's nannism, growth retardation, facial anomalies and immunodeficiency, progeria (Hutchinson-Gilford syndrome), ectrodactyly-ectodermal dysplasia-clefting syndrome, immunodeficiency with absent thumbs, anosmia and ichthyosis, partial albinism, dyskeratosis congenita, Netherton syndrome, anhidrotic ectodermal dysplasia, Papillon-Lefevre syndrome, congenital ichthyosis, acrodermatitis enteropathica, transcobalamin 2 deficiency, Type 1 hereditary orotic aciduria, intractable diarrhea, abnormal facies, trichorrhexis and immunodeficiency, methylmalonic acidemia, biotin dependent carboxylase deficiency, mannosidosis, glycogen storage disease, type 1b, Chediak-Higashi syndrome, familial hypercatabolism, intestinal lymphangiectasia, chronic muco-cutaneous candidiasis, hereditary or congenital hyposplenia or asplenia, Ivermark syndrome.

In one embodiment, the method comprises administering a modulator of a P2Y10 polypeptide to a subject, wherein the modulator has one or more properties selected from the group consisting of (a) the ability to activate a resting T lymphocyte upon association with a P2Y10 polypeptide; (b) the ability to induce expression of a P2Y10 polypeptide on the surface of a resting T lymphocyte upon association with a P2Y10 polypeptide; (c) the ability to stimulate expression of mRNA encoding a P2Y10 polypeptide in a resting T lymphocyte upon association with a P2Y10 polypeptide; and (d) the ability to inhibit proliferation of an activated T lymphocyte upon association with a P2Y10 polypeptide.

The recited properties (a)–(d) are described more fully herein above, which descriptions are applicable in toto to the context of the present method.

Representative P2Y10 modulators are described herein and can be employed in the method. One example of a P2Y10 modulator is an anti-P2Y10 antibody secreted by hybridoma strain PTW-3975. In this example, the antibody can bind specifically to residues 171–191 of P2Y10. Other examples of modulators include small molecules, proteins and nucleic acids. When a P2Y10 modulator is an antibody, the antibody can associate specifically with residues 171–191 of a P2Y10 polypeptide (SEQ ID NOs:3 and 4). Such an antibody can be produced by hybridoma strain PTA-3975, for example.

Various methods of administering a modulator to a subject are known and can be employed in the present method. For example, a modulator can be administered by injection and the injection can be made at any desirable site, such as directly into the subject's circulatory system, or directly into an organ or other internal structure. Other methods of administration are described herein above.

VII.H. Method of Identifying a Modulator of a P2Y10 Polypeptide

Yet an additional aspect of the present invention relates to a method of identifying a modulator of a P2Y10 polypeptide. The method can be employed, for example, in a screening program to identify test molecules that exhibit P2Y10 modulating activity and therefore may be suitable for further development or characterization. In one embodiment, the method comprises (a) measuring the ability of a test molecule to bind to a P2Y10 polypeptide; and (b) measuring one or more of: (i) the ability of the test molecule to activate a resting T lymphocyte; (ii) the ability of the test molecule to induce surface expression of P2Y10 on a T lymphocyte; (iii) the ability of the test molecule to stimulate P2Y10 mRNA expression in a T lymphocyte; and (iv) the ability of the test molecule to inhibit proliferation of an activated T lymphocyte, whereby a test molecule is identified as a modulator if the test molecule binds to a P2Y10 polypeptide and exhibits one or more abilities selected from the group consisting of (i) to (iv).

The ability of a test molecule to bind to a P2Y10 polypeptide can be measured using known binding assays. For example, a test molecule can be detectably labeled (e.g., radiolabeled or fluorescently labeled) and contacted with a P2Y10 polypeptide. Unbound test molecule can then be removed. The ability of the test molecule to bind to a P2Y10 polypeptide can be quantitatively assessed based on the amount of label associated with the P2Y10 polypeptide. When assessing binding of a test compound to a P2Y10 polypeptide, the binding can be assessed relative to a desired degree. That is, binding can be defined by one or more quantitive measurements as described.

Assays for T lymphocyte activation, surface expression of P2Y10 on a T lymphocyte, P2Y10 mRNA expression and T lymphocyte proliferation (and inhibition of proliferation) are known and some of which are described herein. Similar to an assessment of the binding of a test molecule to a P2Y10 polypeptide, the abilities described in (i) to (iv) can be quantitatively assessed relative to a desired set of criteria. For example, a given test compound can be said to possess an ability if it produces an effect recited in (i) to (iv) to a degree that is above or below a selected level.

After performing the above analysis, a test molecule identified as binding a P2Y10 polypeptide to a desired degree (which can be a function of, for example, percent label bound or based on binding constants) and exhibiting one or more properties selected from the group consisting of (i) to (iv) above is identified as a modulator. Modulators identified by employing the method can be employed in the various methods of the present invention.

EXAMPLES

The following Examples have been included to illustrate representative modes of the present invention. Certain aspects of the following Examples are described in terms of techniques and procedures found or contemplated by the present inventors to work well in the practice of the invention. These Examples are exemplified through the use of standard laboratory practices of the inventors. In light of the present disclosure and the general level of skill in the art, those of ordinary skill in the art will appreciate that the following Examples are intended to be exemplary only and that numerous changes, modifications and alterations can be employed without departing from the spirit and scope of the invention.

Example 1

Experimental Procedures for Example 1

Generation of Anti-P2Y10 Monoclonal Antibody (mAb)

An antigenic peptide corresponding to amino acids 171–191 of P2Y10 (SEQ ID NO:3) was synthesized with a carboxy-terminal cysteine for conjugation to KLH (peptide sequence: RSTDLNNNKSCFADLGYKQMNC; SEQ ID NO:4). The KLH-conjugated peptide was used to generate rat anti-P2Y10 monoclonal antibody by immunizing rats, selecting hybridomas as determined by binding to BSA-conjugated antigenic peptide, hybridoma cloning, antibody purification and isotyping using the general procedure published by Starling et al. for the production of rat monoclonal antibodies (Starling et al., (1996) *Eur. J. Immunol.* 26:738–746). The anti-P2Y10 rat hybridoma was deposited with the ATCC Patent Depository (Accession No. PTA-3975, Jan. 11, 2001).

Activation of T cells

Either anti-CD3 (G19-4, Genetic Systems Corporation, Seattle, Wash., USA; see Ledbetter et al., (1986) *J. Immunol.* 136:3945–3952), anti-P2Y10 mAb, or IgG control at 1 µg/mL were immobilized on the surface of 96-well flat-bottom plates (Nalge Nunc, Rochester, N.Y., USA, Cat# 149026) at 4° C. overnight. After washing the plates three times with PBS, human peripheral blood T cells at 2×10$^5$ cells/well were added. Some wells also received anti-CD28 (4 µg/mL, mAb9.3, Fred Hutchinson Cancer Research Center, Seattle, Wash., see Martin et al., (1986) *J. Immunol.* 136:3282–3287), and the cells were incubated at 37° C. for 4 days. Alternatively, phorbol ester (phorbol 12-myristate 13-acetate, Sigma, St. Louis, Mo., USA, Cat # P8139) at a concentration of 100 nM was added to resting T-cells for 30 mins at 37° C.

T-cell Proliferation Assay

Peripheral blood mononuclear cells containing T lymphocytes were activated as described above (some wells also contained anti-P2Y10 at 20 µg/mL). After stimulation at 37° C. for 3 days, [$^3$H]-thymidine (NEN) at a concentration of 5 µCi/mL was added. After an additional 12 hours at 37° C., cells were harvested and the amount of tritium incorporation measured by liquid scintillation counting.

RT-PCR

Total RNA from T cells were isolated using TRIzol (Gibco BRL, Cat #15596), and RT-PCR performed using Gibco's two-step system (SUPERSCRIPTII RNase H reverse transcriptase, Gibco BRL, Cat # 18064, and eLONGase enzymes mix, Cat # 10480). To measure P2Y10 transcription, the following primers were used: CATCT-GCTTCACTCCCTATCA (forward; SEQ ID NO:5) and CATTGATGAACCACTCTCCT (reverse; SEQ ID NO:6). The amplicon resulting from the RT-PCR using these primers corresponds to nucleotides 759–1011 (253 bp) of P2Y10. For GAPDH, the following primers were used: TTAGCAC-CCCTGGCCAAGG (forward; SEQ ID NO:7) and CTTACTCCTTGGAGGCCATG (reverse; SEQ ID NO:8).

Detection of Surface Expression of P2Y10 on T cells by FACS Analysis

Cells were washed with PBS containing FBS (FACS buffer) and then stained by adding anti-P2Y10 mAb (1:100 dilution in FACS buffer) for 30 min on ice. Cells were washed twice with cold FACS buffer followed by addition of mouse anti-rat IgG-FITC (Jackson ImmunoResearch, West Grove, Pa., USA, Cat # 212–096-104) as secondary staining (1:200 dilution) and co-stained with anti-hCD4-PE (Becton Dickinson, 347327, 1:200 dilution), or anti-hCD8-PE (Becton Dickinson, Palo Alto, Calif., USA, Cat # 340046, 1:200 dilution) for 15 mins. After washing twice with cold FACS buffer, cells were resuspended in 0.4 ml cold FACS buffer. FACS analysis performed on a FACSort (Becton Dickinson, Palo Alto, Calif., USA).

Results and Discussion of Example 1

Using the peptide corresponding to amino acids 171–191 of P2Y10 as antigen, a rat anti-P2Y10 monoclonal antibody was identified and isolated. The anti-P2Y10 rat hybridoma has been deposited to the ATCC Patent Depository (No. PTA-3975, Jan. 11, 2001).

The anti-P2Y10 mAb is specific in that it only recognizes a single band of 40 kD molecular weight on Western blots of B cell lysates corresponding to the predicted MW for P2Y10 (see FIG. 1).

Using the anti-P2Y10 mAb, the effect of T cell activation on the surface expression of P2Y10 was investigated by FACS analysis. As shown in Table 1, both CD4+ and CD8+ T cells showed pronounced increases in P2Y10 surface expression when stimulated with either anti-CD-3 alone or anti-CD-3/anti-CD-28 co-stimulation. Phorbol ester (PMA) stimulation also induced P2Y10 surface expression, but to a smaller extent. Surface expression of P2Y10 concomitant with stimulation of T cells suggests a role of P2Y10 in activated T cells. An additional interesting observation was obtained in T cells incubated with the anti-P2Y10 mAb, with the antibody itself appearing to stimulate its own surface expression.

Figure 2:
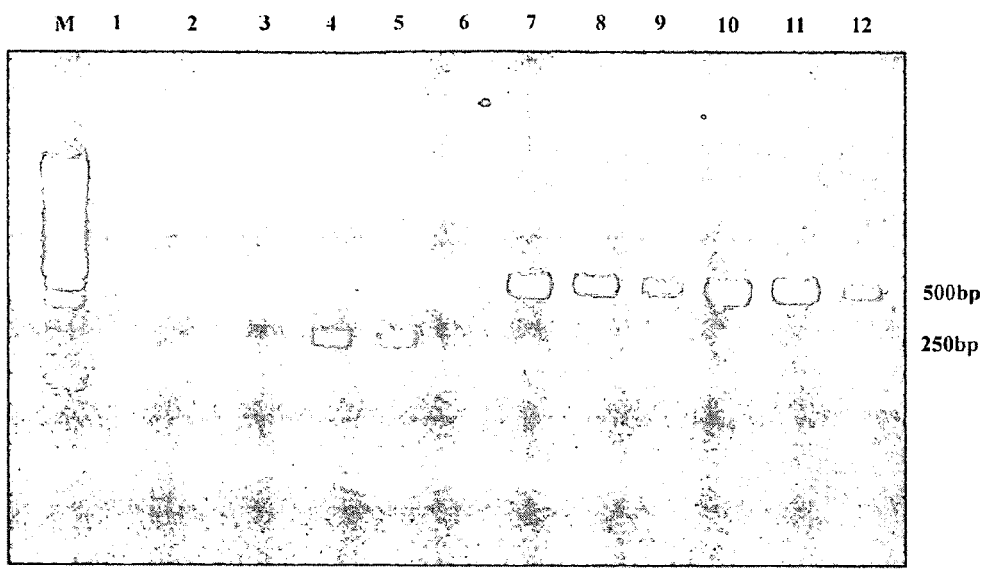
FIG. 2 is a photograph depicting the effect of T cell stimulation on P2Y10 mRNA levels as determined by RT-PCR. P2Y10 primers were used in lanes 1–6, GAPDH primers in lanes 7–12. The treatments were: Lanes 1 & 7, unstimulated cells; lanes 2 & 8, anti-P2Y10-treated cells (1 µg/mL); lanes 3 & 9, anti-P2Y10-treated cells (10 µg/mL); lanes 4 & 10, phorbol ester-treated cells; lanes 5 & 11, anti-CD3-stimulated cells; lanes 6 & 12, anti-CD3/CD28-stimulated cells.

Consistent with these findings, RT-PCR analysis of the amount of mRNA encoding P2Y10 that was induced in T cells stimulated by either phorbol ester, anti-CD3, or anti-CD3/CD28 (see FIG. 2, GAPDH levels are shown as a control for the amount of mRNA). Little message was detected in unstimulated cells. Treatment of the cells with anti-P2Y10 mAb also stimulated P2Y10 mRNA levels. These findings indicate that the stimulation of surface expression of P2Y10 results from stimulation of mRNA encoding P2Y10.

Since P2Y10 expression is coincident with activation and stimulation of T cells, the effect of anti-P2Y10 mAb on T cell proliferation was investigated. As shown in Table 2, anti-CD3 and anti-CD3/CD28 stimulation of T cells resulted in a robust proliferation of T cells as measured by [$^3$H]-thymidine. Interestingly, the presence of the anti-P2Y10 mAb inhibited the proliferation induced by both anti-CD3 and anti-CD3/CD28 stimulation. Interestingly, the anti-P2Y10 mAb alone stimulated T cell proliferation. Consistent with these effects being mediated by binding to P2Y10, a rat IgG isotype control showed little inhibition of T cell proliferation as compared to the anti-P2Y10 mAb (Table 3). Moreover, anti-P2Y10 mAb which had been complexed with the antigenic peptide (amino acids 171–191 of P2Y10) greatly reduced the inhibition of T cell proliferation, thus demonstrating that the effect is P2Y 10-specific.

These results are especially intriguing in that the modulation of P2Y10 by the anti-P2Y10 mAb has opposing effects depending on the state of the T cell. Indeed, resting T lymphocytes are stimulated to proliferate when treated with the anti-P2Y10 mAb alone, and this stimulation regulates its own expression. P2Y10 expression is enhanced upon stimulation of T cells with anti-CD3 or anti-CD3/CD28, but the proliferation of cells is inhibited by the anti-P2Y10 mAb.

Although it is not the inventors' desire to be bound to any theory of operation, the following remarks are submitted. It is unclear how modulation of P2Y10 function by the anti-P2Y10 mAb would regulate these disparate functions. Activation of T cells is a complex process involving a number of receptors including the T cell receptor (TCR), CD3, CD28, LFA-1, CD4, CD2 and CD45R. T cell recognition of an antigenic peptide-MHC complex on an antigen-presenting cell results either in activation and clonal expansion or in a state of nonresponsiveness called clonal anergy. Whether clonal expansion or clonal anergy ensues is determined by the presence or absence of a co-stimulatory signal such as that provided by the CD28/B7 interaction. If a resting $T_H$ cell receives the TCR-mediated signal in the absence of a suitable co-stimulatory signal, then the $T_H$ cell will become anergic. P2Y10 may play a role in the signaling through one or more of these co-stimulatory receptors and regulate the pathways toward expansion versus anergy.

It is also unclear whether the anti-P2Y10 mAb blocks the function of P2Y10 or whether it activates P2Y10 (i.e., an agonistic response). Since the ligand for P2Y10 is unknown, it is difficult to determine the effect of the anti-mAb on the receptor. It may be possible to find a ligand by transfecting cells with recombinant P2Y10 along with a promiscuous G protein such as $G_{\alpha15}$, then screen chemical libraries or tissue homogenates to ascertain whether any P2Y10-dependent cell signaling can be detected. Alternatively, the ability of chemical libraries or tissue homogenates to induce binding of non-hydrolyzable GTP-[γ-S] cell lysates from P2Y10-transfected cells may also be used to screen for ligands. Once an agonist for P2Y10 is identified, then the effect of the anti-P2Y10 mAb on the agonist-induced signaling could be measured to determine whether the mAb blocks the function of the agonist. Even without an agonistic ligand, it may be possible to test the effect of the anti-P2Y10 mAb itself in these systems to monitor for agonistic or antagonistic activity on baseline effects.

Even without knowing whether the anti-P2Y10 mAb antagonizes or agonizes the function of P2Y10, the present results indicate that a modulator of P2Y10 function may have uses in many human disorders. Indeed, modulation of T cell function would have a broad range of possible indications. Disorders that could benefit from a P2Y10 modulator which dampens T cell-dependent immune responses would include rheumatoid arthritis, psoriasis, inflammatory bowel disease, asthma, multiple sclerosis, chronic obstructive pulmonary disorder, systemic lupus erythematosus, and tissue/organ transplant rejection. Disorders that could benefit from a P2Y10 modulator that heightens T cell-dependent immune responses would include cancer, viral infections such as HIV, and bacterial infections.

TABLE 1

P2Y10 surface expression on stimulated T cells as measured by FACS

| Treatment | CD4+ cells | CD8+ cells |
|---|---|---|
| Unstimulated | 1.8%[a] | 1.1%[b] |
| Phorbol ester (PMA) | 3.4% | 1.4% |
| anti-CD3 | 8.7% | 4.9% |
| anti-CD3/anti-CD28 | 6.9% | 5.5% |
| anti-P2Y10 | 9.8% | 9.0% |

[a] The percentage of CD4-positive cells that were also anti-P2Y10-positive.
[b] The percentage of CD4-positive cells that were also anti-P2Y10-positive.

TABLE 2

Effect of Anti-P2Y10 on T cell Proliferation

| Stimulation | Proliferation Ratio (unstimulated = 1)[a] |
|---|---|
| anti-CD3 | 8.0 |
| anti-CD3 + anti-P2Y10 | 2.6 |
| anti-CD3/anti-CD28 | 5.7 |
| anti-CD3/anti-CD28 + anti-P2Y10 | 2.3 |
| anti-P2Y10 | 6.4 |

[a] The amount of [$^3$H]-thymidine incorporation in stimulated cells divided by the amount in unstimulated cells.

TABLE 3

Effect of Antigenic Peptide on Anti-P2Y10 Inhibition of Anti-CD3-induced T cell Proliferation

| Treatment | Inhibition[a] |
|---|---|
| Rat IgG control | 7% |
| anti-P2Y10 | 65% |
| Anti-P2Y10 + antigenic peptide | 17% |

[a] Percent inhibition of the amount of [$^3$H]-thymidine incorporation into anti-CD3-stimulated T cells.

REFERENCES

The references cited in the specification are incorporated herein by reference to the extent that they supplement, explain, provide a background for or teach methodology, techniques and/or compositions employed herein. All cited patents, including patent applications, and publications referred to in this application are herein expressly incorporated by reference. Also expressly incorporated herein by reference are the contents of all citations of GenBank accession numbers, LocusID, and other computer database listings, as well as the contents of the Sequence Listing associated herewith.

It will be understood that various details of the invention may be changed without departing from the scope of the invention. Furthermore, the foregoing description is for the purpose of illustration only.

What is claimed is:

1. An antibody produced by the hybridoma deposited as ATCC PTA-3975.

2. The hybridoma strain deposited as ATCC PTA-3975.

* * * * *